US011058680B2

(12) United States Patent
Toledano

(10) Patent No.: US 11,058,680 B2
(45) Date of Patent: Jul. 13, 2021

(54) COMBINATIONS OF OPIOID/TLR4 ANTAGONISTS AND ACETAMINOPHEN FOR USE IN THE TREATMENT OF EMOTIONAL PAIN AND INSOMNIA

(71) Applicant: Allodynic Threapeutics, LLC, North Miami, FL (US)

(72) Inventor: Annette Channa Toledano, North Miami, FL (US)

(73) Assignee: Allodynie Therapeutics, LLC, North Miami, FL (US)

(*) Notice: Subject to any disclaimer, the term of this patent is extended or adjusted under 35 U.S.C. 154(b) by 0 days.

(21) Appl. No.: 16/365,101

(22) Filed: Mar. 26, 2019

(65) Prior Publication Data

US 2019/0216802 A1    Jul. 18, 2019

Related U.S. Application Data

(62) Division of application No. 15/799,298, filed on Oct. 31, 2017, now abandoned.

(60) Provisional application No. 62/415,300, filed on Oct. 31, 2016.

(51) Int. Cl.
| | |
|---|---|
| *A61K 31/485* | (2006.01) |
| *A61P 25/00* | (2006.01) |
| *A61K 31/167* | (2006.01) |
| *A61K 9/08* | (2006.01) |
| *A61K 9/20* | (2006.01) |
| *A61P 25/30* | (2006.01) |
| *A61P 25/32* | (2006.01) |

(52) U.S. Cl.
CPC .............. *A61K 31/485* (2013.01); *A61K 9/08* (2013.01); *A61K 9/20* (2013.01); *A61K 31/167* (2013.01); *A61P 25/00* (2018.01); *A61P 25/30* (2018.01); *A61P 25/32* (2018.01)

(58) Field of Classification Search
CPC ............................. A61K 31/17; A61K 31/436
See application file for complete search history.

(56) References Cited

U.S. PATENT DOCUMENTS

| | | | |
|---|---|---|---|
| 6,541,478 B1 | 4/2003 | O'Malley et al. | |
| 6,716,449 B2 | 4/2004 | Oshlack et al. | |
| 8,202,525 B2* | 6/2012 | Crain ....................... | A61P 1/00 424/400 |
| 9,095,548 B2 | 8/2015 | Toledano | |
| 9,205,081 B2 | 12/2015 | Toledano | |
| 9,707,225 B2 | 7/2017 | Toledano | |
| 2002/0058673 A1 | 5/2002 | Kaiko et al. | |
| 2003/0022926 A1 | 1/2003 | Lavand Homme | |
| 2004/0024004 A1 | 2/2004 | Sherman et al. | |
| 2005/0038062 A1 | 2/2005 | Burns et al. | |
| 2005/0074493 A1 | 4/2005 | Mehta et al. | |
| 2007/0060500 A1 | 3/2007 | Mickle et al. | |
| 2007/0191350 A1 | 8/2007 | Field et al. | |
| 2007/0259939 A1* | 11/2007 | Stebbing ............... | A61K 31/045 514/282 |
| 2010/0120812 A1 | 5/2010 | Chapleo et al. | |
| 2011/0159048 A1 | 6/2011 | Crain et al. | |
| 2011/0251229 A1 | 10/2011 | Watkins et al. | |
| 2011/0269727 A1 | 11/2011 | Toledano | |
| 2013/0310412 A1 | 11/2013 | Toledano | |
| 2014/0275141 A1* | 9/2014 | Toledano ............... | A61K 31/485 514/282 |
| 2014/0275142 A1 | 9/2014 | Toledano | |
| 2014/0296274 A1 | 10/2014 | Toledano | |
| 2014/0296275 A1 | 10/2014 | Toledano | |
| 2016/0051537 A1 | 2/2016 | Toledano | |
| 2016/0158222 A1 | 6/2016 | Toledano | |
| 2017/0319577 A1 | 11/2017 | Toledano | |

FOREIGN PATENT DOCUMENTS

| | | | | |
|---|---|---|---|---|
| EP | 1813283 A1 | 8/2007 | | |
| WO | 1999032119 A1 | 7/1999 | | |
| WO | 9945906 A1 | 9/1999 | | |
| WO | WO-9945906 A1 * | 9/1999 | ......... | A61K 31/4515 |
| WO | 2008008380 A1 | 1/2008 | | |
| WO | 2009059048 A2 | 5/2009 | | |
| WO | 2012048294 A2 | 4/2012 | | |
| WO | 2014160077 A1 | 10/2014 | | |

OTHER PUBLICATIONS

Kim (Society of Biological Psychiatry vol. 49 pp. 914-921 published 2001) (Year: 2001).*
Bowling (2009) "Low-Dose Naltrexone (LON). The '411' on LON," Momentum Magazine: A National Multiple Sclerosis Society Publication. 44-46.
Breivik et al. (2008) "Assesment of pain," Br. J. Anaesth. 101 (1):17-24.
De Marinis et al. (1991) "Headache in the use and withdrawal of opiates and other associated substances of abuse," Headache: The Journal of Head and Face Pain. 31(3):159-163.
Franceschini et al. (Jan. 11, 2013) "TNFa Levels and Macrophages Expression Reflect an Inflammatory Potential of Trigeminal Ganglia in a Mouse Model of Familial Hemiplegic Migraine," PLoS One. 8(1):e52394.
Hersch et al. (May 1993) "Narcotic receptor blockade and its effect on the analgesic response to placebo and ibuprofen after oral surgery," Oral Surgery, Oral Medicine, Oral Pathology. 75(5):539-546.
Hutchinson et al. (2007) "Opiod-induced glial activation: mechanisms of activation and implications for opiod analgesia, dependence, and reward," Sci. World. J. 7:98-111.

(Continued)

*Primary Examiner* — Theodore R. Howell
*Assistant Examiner* — George W Kosturko
(74) *Attorney, Agent, or Firm* — Ted Whitlock; Santucci Priore, PL

(57) ABSTRACT

Disclosed are compositions for the treatment of emotional pain, physical pain, and insomnia comprising a compound comprising an opioid antagonist that treats pain by blocking Toll-like receptor 4 (TLR4). Examples of opioid antagonist include naltrexone and naloxone, and their use in the treatment, prevention, and reversal of pain.

16 Claims, 1 Drawing Sheet

(56) References Cited

OTHER PUBLICATIONS

Hutchinson et al. (2008) "Minocycline suppresses morphine-induced respiratory depression, suppresses morphine-induced reward, and enhances systemic morphine-induced analgesia," Brain, Behavior, and Immunity. 22(8):1248-1256.
Hutchinson et al. (2008) "Non-stereoselective reversal of neuropathic pain by naloxone and naltrexone: involvement of toll-like receptor 4 (TLR4)," Eur. J. Neurosci. 28:20-29.
Hutchinson et al. (2008) "Proinflammatory cytokines oppose opioid-induced acute and chronic analgesia," Brain, Behavior, and Immunity. 22(8):1178-1189.
Hutchinson et al. (May 19, 2010) "Possible involvement of toll-like receptor 4/myeloid differentiation factor-2 activity of opiod inactive isomers causes spinal proinflammation and related behavioral consequences," Neuroscience. 167(3):880-893.
International Search Report with Written Opinion corresponding to International Patent Application No. PCT/US2014/025771, dated Aug. 26, 2014, 26 pages.
Johnston et al. (2004) "A Role for Proinflamatory Cytokines and Fractalkine in Analgesia, Tolerance, and Subsequent Pain Facilitation Induced by Chronice Intrathecal Morphine," J. Neurosci. 24(33):7353-7365.
Komatsu et al. (2009) "Mechanism of allodynia evoked by intrathecal morphine-3-glucuronide in mice," Int. Rev. NeuroBiol. 85:207-219.
Kumar et al. (2003) "Gabapentin in the management of pentazocine dependence: a potent analgesic-anticraving gent," J. Assoc. Physicians India. 51:673-676.
Lewis et al. (Jan. 20, 2010) "Evidence that intrathecal morphine-3-glucuronide may cause pain enhancement via toll-like receptor 4/MD-2 and interleukin-1beta," Neuroscience. 165(2):569-583.
Mannelli (2006) "Antagonist treatment of opiod withdrawal translational low dose approach," J. Addict. Dis. 25(2):1-8.
Milligan et al. (2009) "Pathological and protective roles of glia in chronic pain," Nat. Rev. Neurosci. 10(1):23-26.
Nasu-Tada et al. (2006) "Possible involvement of increase in spinal fibronectin following peripheral nerve injury in upregulation of microglial P2X4, a key molecule for mechanical allodynia," Glia. 53:769-775.
Ngian et al. (Feb. 2011) "The use of opioids in fibromyalgia," Int. J. Rheum. Dis. 14(1):6-11.
Novella (May 5, 2010) "Low Dose Naltrexone—Bogus or Cutting Edge Science?" Science Based Medicine. Accessible on the Internet at URL: <https://www.sciencebasedmedicine .org/low-dose-naltrexo ne-bogus-or-cutting-edqe-science/> [Last Accessed May 29, 2015].
Obata et al. (2008) "Toll-like receptor 3 contributes to spinal glial activation and tactile allodvnia after nerve iniurv." J. Neurochem. 105:2249-2259.
Ploesser et al. (Mar. 2010) "Low Dose Naltrexone: Side Effects and Efficacy in Gastrointestinal Disorders," International Journal of Pharmaceutical Compounding. 14(2)171-173.
Romero-Sandoval et al. (2008) "Neuroimmune interactions and pain: focus on qlial-modulatinq tarqets," Curr. Opin. Investiq. Druqs. 9:726-734.
Serajuddin (2007) "Salt Formation to Improve Drug Solubility," Advanced Drug Delivery Reviews. 59:603-616.
Tanga et al. (2005) "The CNS role of Toll-like receptor 4 in innate neuroimmunity and painful neuropathy," Proc. Natl. Acad. Sci. 102:5856-5861.
Turk et al. (2004) "What should be the core outcomes in chronic pain clinical trials?" Arthritis Res. Ther. 6(4):151-154.
Vining et al. (1988) "Clinical Utility of Rapid Clonidine—Naltrexone Detoxification for O ioid Abusers," British Journal of Addiction. 83(5):567-575.
Watkins et al. (2009) "The 'toll' of opioid-induced glial activation: improving the clinical efficacy of opioids by targeting glia," Trends in Pharmacological Sciences. 30(11):581-591.
Way et al. (1998) "Opioid Analgesics & Antagonists," Basic and Clinical Pharmacology. 7:496-515.
Webster (2007) "Oxytrex: an oxycodone and ultra-low-dose naltrexone formulation," Expert Opin. Investig. Drugs. 16 (8):1277-1283.
Younger et al. (2009) "Fibromyalgia Symptoms Are Reduced by Low-Dose Naltrexone: A Pilot Study," Pain Medicine. 10(4):663-672.
Anton et al. (2011) "Gabapentin Combined with Naltrexone for the Treatment of Alcohol Dependence," Am. J. Psychiatry. 168:709-717.
Bryans et al. (1999) "3-Substituted GABA Analogs with Central Nervous System Activity: A Review," Med. Res. Rev. 19:149-177.
Martinotti et al. (2010) "Pregabalin versus naltrexone in alcohol dependence: a randomised, double-blind, comparison trial," J. Psvchopharmacol. 24:1367-1374.
Mikawa et al. (1996) "Oral Clonidine Premedication Reduces Postoperative Pain in Children," Anesth. Analg. 82:225-230.
United States Food and Drug Administration (Oct. 8, 2013) "REVIA Naltrexone Hydrochloride Tablets USP," Opioid Antagonist. Accessible on the Internet at URL: <https://www.accessdata.fda.gov/drugsatfda_docs/label/2013/018932s017lbl.p df> [Last Accessed Apr. 4, 2016].
Hinz et al. (2008) "Acetaminophen (paracetamol) is a selective cyclooxygenase-2 inhibitor in man," The FASEB Journal. 22(2):383-390.
Kanazi et al. (2006) "Effects of low-dose dexmedetomidine or clonidine on the characteristics of bupivacaine on spinal block," Acta Anaesthesiol. Scand. 50:222-227.

* cited by examiner

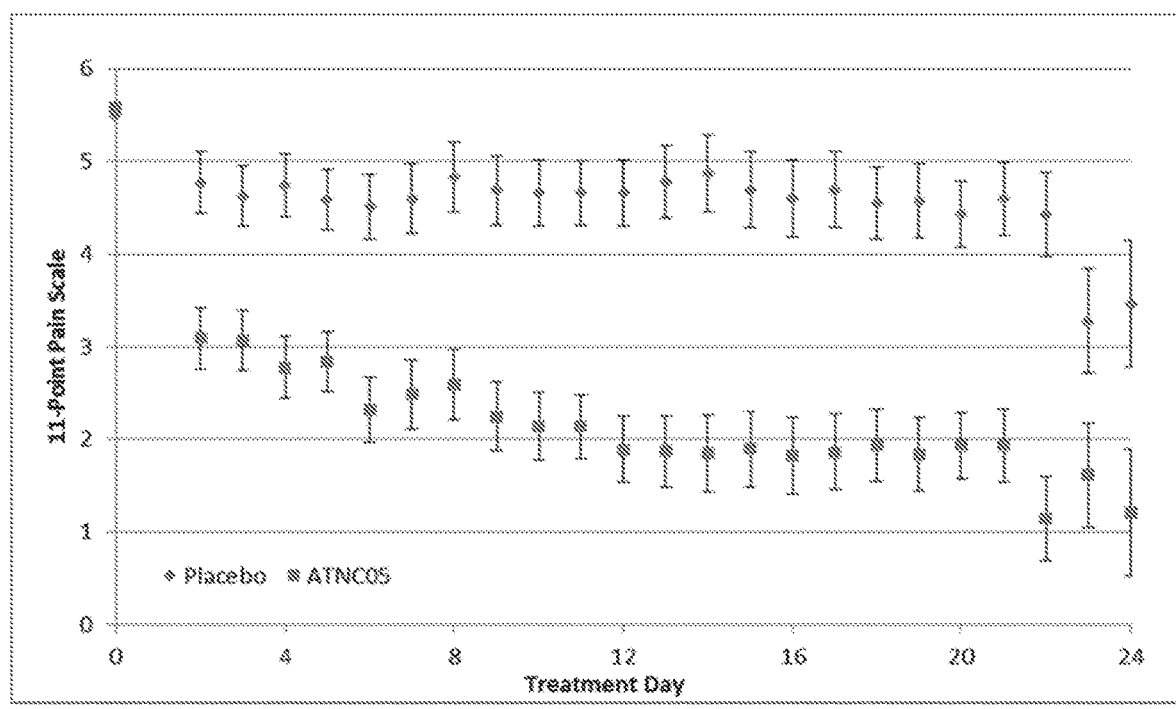

COMBINATIONS OF OPIOID/TLR4 ANTAGONISTS AND ACETAMINOPHEN FOR USE IN THE TREATMENT OF EMOTIONAL PAIN AND INSOMNIA

CROSS-REFERENCE TO RELATED APPLICATIONS

This is a divisional of U.S. patent application Ser. No. 15/799,298, filed Oct. 31, 2017, which claims the benefit of U.S. Provisional Patent Application, Ser. No. 62/415,300, both of which are incorporated herein by reference in their entirety.

FIELD

This invention relates to compositions comprising an opioid/TLR4 antagonist and acetaminophen for the treatment, prevention, and reversal of physical and emotional pain.

BACKGROUND

"Physical pain and social pain—may rely on some of the same behavioral and neural mechanisms that register pain-related affect. Overlapping social and physical pain systems probably conferred an advantage among our evolutionary ancestors and the social attachment system in humans may have evolved by piggybacking directly onto the physical pain system to promote survival" (DeWall C. N., et al., Acetaminophen (also referred to herein as acetyl-para-aminophenol or APAP) reduces social pain: Behavioral and neural evidence. Psychological Science, 21, 931-937 (2010).).

Given benzodiazepines and opioids both depress the central nervous system and can decrease respiratory drive, concurrent use might put patients at greater risk for fatal overdose. A drug that can reduce reliance on opioid medications and benzodiazepines, and also help avoid the risk of overdose associated with co-prescription of opioids with benzodiazepines is valuable.

Thus, there is a need in the art for therapies that can safely and effectively treat physical pain and emotional pain, in certain circumstances, at the same time. Described herein is a novel approach for the treatment of pain, and in particular, the treatment of emotional pain, physical pain, and insomnia. Specific drugs and combinations of drugs and the dosages needed to treat pain (physical and emotional) and insomnia is the subject of the instant invention.

SUMMARY

The disclosure provides a method of use of an opioid/TLR4 antagonist, or a pharmaceutically acceptable salt or solvate thereof, for treating emotional pain in a mammal, such as a human. The opioid/TLR4 antagonist is selected from the group consisting of naltrexone, norbinaltorphimine, nalmefene, naloxone, nalorphine, methylnaltrexone, samidorphan, cyprodime, naltrindole, amentoflavone, naltriben, norbinaltorphimine, 6-β-naltrexol, metabolites and pro drugs thereof, or pharmaceutically acceptable salts or solvates of any thereof. In an embodiment, the opioid/TLR4 antagonist is naltrexone, or a pharmaceutically acceptable salt or solvate thereof.

In another embodiment, the opioid/TLR4 antagonist is (+)-naltrexone (dextro-naltrexone), as well as appropriate mixtures thereof, as well as pro drugs thereof, or pharmaceutically acceptable salts or solvates thereof.

In an embodiment, the method of treating emotional pain comprises administering naltrexone, or a pharmaceutically acceptable salt or solvate thereof, to the mammal at between about 0.25 mg to 15 mg per day.

In another embodiment, the method of treating emotional pain comprises administering naltrexone, or a pharmaceutically acceptable salt or solvate thereof, to the mammal at about 1.5 mg per day.

In another embodiment, the method of treating emotional pain comprises administering naltrexone, or a pharmaceutically acceptable salt or solvate thereof, to the mammal at about 2.25 mg per day.

In another embodiment, the method of treating emotional pain comprises administering naltrexone, or a pharmaceutically acceptable salt or solvate thereof, to the mammal at about 3.25 mg per day.

In another embodiment, the method of treating emotional pain comprises administering naltrexone, or a pharmaceutically acceptable salt or solvate thereof, to the mammal at about 5 mg per day.

In another embodiment, the method of treating emotional pain comprises administering naltrexone, or a pharmaceutically acceptable salt or solvate thereof, to the mammal at about 6.75 mg per day.

In another embodiment, the method of treating emotional pain comprises administering naltrexone, or a pharmaceutically acceptable salt or solvate thereof, to the mammal at about 9 mg per day.

In another embodiment, the method of treating emotional pain comprises administering naltrexone, or a pharmaceutically acceptable salt or solvate thereof, to the mammal at about 15 mg per day.

In another embodiment, the method of treating emotional pain comprises administering naltrexone, or a pharmaceutically acceptable salt or solvate thereof, once, twice, three or four times per day.

In another embodiment, the method of treating emotional pain comprises administering naltrexone, or a pharmaceutically acceptable salt or solvate thereof, systemically, including but not limited to mucosal, nasal, oral, parenteral, gastrointestinal, topical, or sublingual routes.

In an embodiment, the naltrexone, or pharmaceutically acceptable salt or solvate thereof, is formulated into a single fixed dosage form. In another embodiment, the single dosage form is in the form of tablets, lozenges, troches, hard candies, or liquids.

In an embodiment, the invention provides a method for treating emotional pain comprising administering naltrexone, or a pharmaceutically acceptable salt or solvate thereof, wherein the emotional pain is associated with a pathology consisting of adjustment disorder.

In another embodiment, the invention provides a method for treating emotional pain comprising administering naltrexone, or a pharmaceutically acceptable salt or solvate thereof, wherein the emotional pain is associated with an adjustment disorder, and wherein the adjustment disorder is emotional disturbance.

In another embodiment, the invention provides a method for treating emotional pain comprising administering naltrexone, or a pharmaceutically acceptable salt or solvate thereof, wherein the emotional pain is associated with emotional disturbance, which is shown in one or more signs or symptoms selected from the group consisting of abandonment, ambivalence, anger, anguish, anxiety, betrayal, compulsion, confusion, despair, deterioration, emptiness, failure, fatigue, fear, frustration, grief, guilt, helplessness, hopelessness, horror, hurt feelings, inferiority, insomnia, irritation, loneliness, loss of meaning, lure of death, powerlessness, rejection, sadness, self-hate, shame, stress, terror, ruminations, and worthlessness.

In another embodiment, the invention provides a method for treating emotional pain in a mammal comprising administering naltrexone, or a pharmaceutically acceptable salt or solvate thereof, wherein the mammal is also experiencing one or more substance abuse or addiction selected from drug abuse, drug addiction, alcohol abuse, and alcohol addiction.

In another embodiment, the invention provides a method for treating emotional pain in a mammal comprising administering naltrexone, or a pharmaceutically acceptable salt or solvate thereof, wherein the mammal is not experiencing a substance abuse or addiction selected from drug abuse, drug addiction, alcohol abuse, and alcohol addiction.

Another embodiment of the disclosure is a method for treating emotional pain in a mammal that is also experiencing physical pain comprising administering naltrexone, or a pharmaceutically acceptable salt or solvate thereof, wherein the method is also effective for the treatment of the physical pain.

In another embodiment, the invention provides a method for treating emotional pain in a mammal that is also experiencing physical pain comprising administering naltrexone, or a pharmaceutically acceptable salt or solvate thereof, wherein the physical pain is selected from the group consisting of neuropathic pain, nociceptive pain, nociceptive pain with an allodynic component, low back pain, migraine, inflammation, osteoarthritis, rheumatoid arthritis, psoriatic arthritis, trigeminal neuralgia, vulvodynia, irritable bowel syndrome, post herpetic neuralgia, and diabetic neuropathy.

Another embodiment of the disclosure is a method for treating emotional pain in a mammal that is also experiencing insomnia comprising administering naltrexone, or a pharmaceutically acceptable salt or solvate thereof, wherein the method is also effective for the treatment of the insomnia.

Another embodiment of the disclosure is a method for treating emotional pain in a mammal that is also experiencing insomnia and physical pain comprising administering naltrexone, or a pharmaceutically acceptable salt or solvate thereof. In certain embodiments, the dose range of naltrexone is administered to the mammal at a dose from about 0.25 mg to about 50 mg per day. In other embodiments, acetaminophen is also administered to the mammal. In certain embodiments, the dose range of the acetaminophen is administered to the mammal at a dose from about 325 mg to about 4000 mg per day. In certain embodiments, the dose range of the acetaminophen is administered to the mammal at a dose from about 325 mg to about 2000 mg per day.

Another embodiment of the disclosure is a method for treating emotional pain in a mammal in need thereof comprising administering to said mammal a combination of a first compound comprising an opioid/TLR4 antagonist, or a pharmaceutically acceptable salt or solvate thereof, and a second compound comprising acetaminophen, or a pharmaceutically acceptable salt or solvate thereof. The opioid/TLR4 antagonist is selected from the group consisting of naltrexone (NTX), norbinaltorphimine, nalmefene, naloxone, nalorphine, methylnaltrexone, samidorphan, cyprodime, naltrindole, amentoflavone, naltriben, norbinaltorphimine, 6-β-naltrexol, metabolites and pro drugs thereof, or pharmaceutically acceptable salts or solvates of any thereof.

In an embodiment, the opioid/TLR4 antagonist is naltrexone, or a pharmaceutically acceptable salt or solvate thereof.

In another embodiment, the opioid/TLR4 antagonist is naltrexone in a sustained release formulation. In another embodiment, the opioid/TLR4 antagonist is (+)-naltrexone (dextro-naltrexone), as well as appropriate mixtures thereof, as well as pro drugs thereof, or pharmaceutically acceptable salts or solvates thereof.

In another embodiment, the method of treating emotional pain comprises administering the naltrexone, or a pharmaceutically acceptable salt or solvate thereof, at from about 0.25 mg to about 50 mg per day, and administering the acetaminophen, or a pharmaceutically acceptable salt or solvate thereof, at between about 325 mg to 4000 mg per day.

In another embodiment, the method of treating emotional pain comprises administering the naltrexone, or a pharmaceutically acceptable salt or solvate thereof, at about 1.5 mg per day, and administering the acetaminophen, or pharmaceutically acceptable salt or solvate thereof, at about 325 mg per day.

In another embodiment, the method of treating emotional pain comprises administering the naltrexone, or a pharmaceutically acceptable salt or solvate thereof, at about 2.25 mg per day, and administering the acetaminophen, or pharmaceutically acceptable salt or solvate thereof, at about 325 mg per day.

In another embodiment, the method of treating emotional pain comprises administering the naltrexone, or a pharmaceutically acceptable salt or solvate thereof, at about 3.25 mg per day, and administering the acetaminophen, or pharmaceutically acceptable salt or solvate thereof, at about 325 mg per day.

In another embodiment, the method of treating emotional pain comprises administering the naltrexone, or a pharmaceutically acceptable salt or solvate thereof, at about 5 mg per day, and administering the acetaminophen, or pharmaceutically acceptable salt or solvate thereof, at about 325 mg per day.

In another embodiment, the method of treating emotional pain comprises administering the naltrexone, or a pharmaceutically acceptable salt or solvate thereof, at about 4.5 mg per day, and administering the acetaminophen, or pharmaceutically acceptable salt or solvate thereof, at about 650 mg per day.

In another embodiment, the method of treating emotional pain comprises administering the naltrexone, or a pharmaceutically acceptable salt or solvate thereof, at about 6.75 mg per day, and administering the acetaminophen, or pharmaceutically acceptable salt or solvate thereof, at about 975 mg per day.

In another embodiment, the method of treating emotional pain comprises administering the naltrexone, or a pharmaceutically acceptable salt or solvate thereof, at about 9 mg per day, and administering the acetaminophen, or pharmaceutically acceptable salt or solvate thereof, at about 1300 mg per day.

In another embodiment, the method of treating emotional pain comprises administering the naltrexone, or a pharmaceutically acceptable salt or solvate thereof, at about 15 mg per day, and administering the acetaminophen, or pharmaceutically acceptable salt or solvate thereof, at about 2000 mg per day.

In another embodiment, the method of treating emotional pain with the combination of naltrexone and acetaminophen comprises administering the compound once, twice, three or four times per day.

In another embodiment, the method of treating emotional pain with the combination of naltrexone and acetaminophen comprises administering the compound systemically, including but not limited to mucosal, nasal, oral, parenteral, gastrointestinal, topical or sublingual routes.

In an embodiment, the combination of naltrexone and acetaminophen is formulated into a single fixed dosage form. In another embodiment, the single dosage form is in the form of tablets, lozenges, troches, hard candies, liquid, powders, sprays, creams, salves or suppositories.

In an embodiment, the invention provides a method for treating emotional pain with a combination of naltrexone and acetaminophen, wherein the emotional pain is associated with a pathology consisting of adjustment disorder the stressor may have affected the integrity of an individual's social network (bereavement, separation experiences").

In another embodiment, the invention provides a method for treating emotional pain associated with adjustment disorder with a combination of naltrexone and acetaminophen, wherein the adjustment disorder is emotional disturbance.

In another embodiment, the invention provides a method for treating emotional pain associated with adjustment disorder with a state of emotional disturbance with a combination of naltrexone and acetaminophen, wherein the emotional disturbance is shown in one or more signs or symptoms selected from the group consisting of abandonment, ambivalence, anger, anguish, anxiety, betrayal, compulsion, confusion, despair, deterioration, emptiness, failure, fatigue, fear, frustration, grief, guilt, helplessness, hopelessness, horror, hurt feelings, inferiority, insomnia, irritation, loneliness, loss of meaning, lure of death, powerlessness, rejection, sadness, self-hate, shame, stress, terror, ruminations, and worthlessness.

In another embodiment, the invention provides a method for treating emotional pain in a mammal with a combination of naltrexone and acetaminophen, wherein the mammal is also experiencing one or more substance abuse or addiction selected from drug abuse, drug addiction, alcohol abuse, and alcohol addiction.

In another embodiment, the invention provides a method for treating emotional pain in a mammal with a combination of naltrexone and acetaminophen, wherein the mammal is not experiencing a substance abuse or addiction selected from drug abuse, drug addiction, alcohol abuse, and alcohol addiction.

Another embodiment of the disclosure is a method for treating emotional pain in a mammal that is also experiencing physical pain with a combination of naltrexone and acetaminophen, wherein the method is also effective for the treatment of the physical pain.

In another embodiment, the invention provides a method for treating emotional pain in a mammal that is also experiencing physical pain with a combination of naltrexone and acetaminophen, wherein the physical pain is selected from the group consisting of neuropathic pain, nociceptive pain, nociceptive pain with an allodynic component, low back pain, migraine, inflammation, osteoarthritis, rheumatoid arthritis, psoriatic arthritis, trigeminal neuralgia, vulvodynia, irritable bowel syndrome, post herpetic neuralgia, and diabetic neuropathy.

Another embodiment of the disclosure is a method for treating emotional pain in a mammal that is also experiencing insomnia with a combination of naltrexone and acetaminophen, wherein the method is also effective for the treatment of the insomnia.

Another embodiment of the disclosure is a method for treating emotional pain in a mammal in need thereof comprising administering to said mammal a combination of a first compound comprising naltrexone, or a pharmaceutically acceptable salt or solvate thereof, wherein the naltrexone or pharmaceutically acceptable salt or solvate thereof is administered to the mammal at about 1.5 mg per day, and a second compound comprising acetaminophen, or a pharmaceutically acceptable salt or solvate thereof, wherein the acetaminophen or pharmaceutically acceptable salt or solvate thereof is administered to the mammal at about 325 mg per day.

Another embodiment of the disclosure is a method for treating emotional pain in a mammal in need thereof comprising administering to said mammal a combination of a first compound comprising naltrexone, or a pharmaceutically acceptable salt or solvate thereof, wherein the naltrexone or pharmaceutically acceptable salt or solvate thereof is administered to the mammal at about 3.25 mg per day, and a second compound comprising acetaminophen, or a pharmaceutically acceptable salt or solvate thereof, wherein the acetaminophen or pharmaceutically acceptable salt or solvate thereof is administered to the mammal at about 325 mg per day.

Another embodiment of the disclosure is a method for treating emotional pain in a mammal in need thereof comprising administering to said mammal a combination of a first compound comprising naltrexone, or a pharmaceutically acceptable salt or solvate thereof, wherein the naltrexone or pharmaceutically acceptable salt or solvate thereof is administered to the mammal at about 5 mg per day, and a second compound comprising acetaminophen, or a pharmaceutically acceptable salt or solvate thereof, wherein the acetaminophen or pharmaceutically acceptable salt or solvate thereof is administered to the mammal at about 325 mg per day In certain embodiments, the invention provides a method for treating physical pain in a mammal with a composition comprising a combination of naltrexone and acetaminophen, wherein the physical pain is selected from the group consisting of neuropathic pain, nociceptive pain, nociceptive pain with an allodynic component, low back pain, migraine, inflammation, osteoarthritis, rheumatoid arthritis, psoriatic arthritis, trigeminal neuralgia, vulvodynia, irritable bowel syndrome, post herpetic neuralgia, and diabetic neuropathy.

BRIEF DESCRIPTION OF THE FIGURES

FIG. 1 is a graph depicting the Average Pain Intensity (API) by day over a three-week treatment period for chronic low back patients (CLBP) treated with a combination of naltrexone and clonidine.

DETAILED DESCRIPTION

The methods disclosed herein will now be described more fully. The methods described should not be construed as limited to the embodiments set forth herein. Rather, these embodiments are provided so that this disclosure will be thorough and complete, and will fully convey the scope of this work to those skilled in the art.

The disclosure provides methods of treating emotional pain in a patient experiencing emotional pain. In an aspect, the methods include the administration of an opioid/TLR4 antagonist, or a pharmaceutically acceptable salt or solvate thereof.

The proposed method of treatment inhibits release of pro-inflammatory cytokines via toll-like receptor 4 (TLR4) pathway blockade and inhibits TLR4-induced COX-2 expression with use of a TLR4 antagonist and acetaminophen, (a highly selective cyclooxygenase-2 (COX-2) inhibitor). The treatment method reverses neuroinflammation processes that cause neuropathic pain, migraine, and emotional pain by dually blocking pro-inflammatory cytokines release and COX-2 activation.

After tissue injury or cellular stress, TLR4 detects and reacts to endogenous ligands known as danger-associated molecular patterns (DAMPs). Activation of the TLR4 pathway in the glia induces release of pro-inflammatory cytokines [nitric oxide (NO), tumor necrosis factor-α (TNF-α), and reactive oxygen species (ROS)] and expression of COX-2 (the TLR4-COX-2-PGE2 axis) causing glial activation which causes neuro-inflammation nearby spinal nerve roots and trigeminal nerve neurons leadings to back pain and migraines (in predisposed individuals). Suppressing TLR4 and inhibiting COX-2 expression simultaneously, correlates with neuropathic pain, migraine, and emotional pain relief.

The TLR4 antagonist blocks the TLR4 signaling cascade from releasing proinflammatory cytokines, while acetaminophen adds a second action of blocking the TLR4 induced COX-2 activation. The TLR4 antagonist delivers the first action while acetaminophen delivers a second action, (a one-two punch), in doing so, overturning the consequences of TLR4 cascade activation.

In certain embodiments, the opioid TLR4 antagonist is selected from naltrexone, norbinaltorphimine, nalmefene, naloxone, nalorphine, methylnaltrexone, samidorphan, cyprodime, naltrindole, amentoflavone, naltriben, norbinaltorphimine, 6-β-naltrexol, metabolites and pro drugs thereof, or pharmaceutically acceptable salts or solvates of any thereof.

In certain embodiments, the opioid TLR4 antagonist is naltrexone. In other embodiments, the naltrexone is (+)-naltrexone (dextro-naltrexone). It has been shown, herein, that naltrexone is unexpectedly effective in the treatment of emotional pain.

In certain embodiments, the naltrexone, or a pharmaceutically acceptable salt or solvate thereof, is administered to the mammal from about 0.25 mg to about 50 mg per day. In certain embodiments, the naltrexone, or a pharmaceutically acceptable salt or solvate thereof, is administered to the mammal at from about 1.5 to about 10 mg per day. In certain embodiments, the naltrexone, or a pharmaceutically acceptable salt or solvate thereof, is administered to the mammal at from about 2.25 to about 30 mg per day. In certain embodiments, the naltrexone, or a pharmaceutically acceptable salt or solvate thereof, is administered to the mammal at from about 3.25 to about 40 mg per day. In certain embodiments, the naltrexone, or a pharmaceutically acceptable salt or solvate thereof, is administered to the mammal at from about 5.0 to about 50 mg per day.

In certain embodiments, the naltrexone, or a pharmaceutically acceptable salt or solvate thereof, is administered to the mammal at from about 0.25 to about 1, from about 1.1 to about 1.4, from about 1.5 to about 2, from about 2.5 to about 3.5, from about 4.0 to about 5.0, from about 6.0 to about 7.5, from about 8.0 to about 10, from about 11 to about 15, from about 16 to about 20, from about 21 to about 25, from about 26 to about 30, from about 31 to about 35, from about 36 to about 40, from about 41 to about 45, or from about 46 to about 50, from about mg per day.

In certain embodiments, the naltrexone, or a pharmaceutically acceptable salt or solvate thereof, is administered to the mammal at about 1.5 mg per day. In certain embodiments, the naltrexone, or a pharmaceutically acceptable salt or solvate thereof, is administered to the mammal at about 2.25 mg per day. In certain embodiments, the naltrexone, or a pharmaceutically acceptable salt or solvate thereof, is administered to the mammal at about 3.25 mg per day. In certain embodiments, the naltrexone, or a pharmaceutically acceptable salt or solvate thereof, is administered to the mammal at about 5 mg per day. In certain embodiments, the naltrexone, or a pharmaceutically acceptable salt or solvate thereof, is administered to the mammal at about 9 mg per day. In certain embodiments, the naltrexone, or a pharmaceutically acceptable salt or solvate thereof, is administered to the mammal at about 15 mg per day.

In certain embodiments, the naltrexone, or a pharmaceutically acceptable salt or solvate thereof, is administered once, twice, three, or four times per day.

As used herein, "administered from about X to about Y mg" means that the referred to substance is administered at any value within the stated range including the endpoints of the range. For example, "the dose of naltrexone administered to the patient is from 0.25 mg to 50 mg," includes administration of 0.25 mg of naltrexone, 50 mg of naltrexone and all doses in between.

As used herein, the term "about" refers to a range of values±5% of a specified value. For example, the phrase "about 100" includes±5% of 100, or from 95 to 105.

In another aspect, the methods include the administration of an opioid TLR4 antagonist or a pharmaceutically acceptable salt thereof in combination with acetaminophen, or a pharmaceutically acceptable salt or solvate thereof.

In certain embodiments, acetaminophen, or a pharmaceutically acceptable salt or solvate thereof, is administered in combination with an opioid TLR4 antagonist, or a pharmaceutically acceptable salt or solvate thereof, from about 300 to about 2000 mg per day. In certain embodiments, acetaminophen or pharmaceutically acceptable salt or solvate thereof is administered in combination with an opioid TLR4 antagonist, or a pharmaceutically acceptable salt or solvate thereof, at from about 300 to about 350, from about 600 to about 700, from about 900 to about 1050, from about 1200 to about 1300, and from about 1250 to about 2000 mg per day.

In certain embodiments, acetaminophen is administered in combination with an opioid TLR4 antagonist selected from naltrexone, norbinaltorphimine, nalmefene, naloxone, nalorphine, methylnaltrexone, samidorphan, cyprodime, naltrindole, amentoflavone, naltriben, norbinaltorphimine, 6-β-naltrexol, metabolites and pro drugs thereof, or pharmaceutically acceptable salts or solvates of any thereof.

In certain embodiments, the opioid TLR4 antagonist is naltrexone. In other embodiments, the naltrexone is in a sustained release formulation. In other embodiments, the naltrexone is (+)-naltrexone (dextro-naltrexone).

In certain embodiments, the naltrexone, or a pharmaceutically acceptable salt or solvate thereof, is administered to the mammal at between about 0.25 mg to 50 mg per day, and the acetaminophen, or a pharmaceutically acceptable salt or solvate thereof, is administered to the mammal at between about 325 mg to 4000 mg per day.

In certain embodiments, the naltrexone, or a pharmaceutically acceptable salt or solvate thereof, is administered to the mammal at about 1.5 mg per day, and the acetaminophen, or a pharmaceutically acceptable salt or solvate thereof, is administered to the mammal at about 325 mg per day. In certain embodiments, the naltrexone, or a pharmaceutically acceptable salt or solvate thereof, is administered to the mammal at about 2.25 mg per day, and the acetaminophen, or a pharmaceutically acceptable salt or solvate thereof, is administered to the mammal at about 325 mg per day. In certain embodiments, the naltrexone, or a pharmaceutically acceptable salt or solvate thereof, is administered to the mammal at about 3.25 mg per day, and the acetaminophen, or a pharmaceutically acceptable salt or solvate thereof, is administered to the mammal at about 325 mg per day.

In certain embodiments, the naltrexone, or a pharmaceutically acceptable salt or solvate thereof, is administered to the mammal at about 9 mg per day, and the acetaminophen, or a pharmaceutically acceptable salt or solvate thereof, is administered to the mammal at about 1300 mg per day. In certain embodiments, the naltrexone, or a pharmaceutically acceptable salt or solvate thereof, is administered to the mammal at about 15 mg per day, and the acetaminophen, or a pharmaceutically acceptable salt or solvate thereof, is administered to the mammal at about 2000 mg per day.

In certain embodiments, the naltrexone and acetaminophen are administered at a ratio that ranges from 1:500 to 3:200. In certain embodiments, the naltrexone and acetaminophen are administered at a ratio that ranges from 2-2.5:325. In certain embodiments, the naltrexone and acetaminophen are administered at a ratio that ranges from 3-3.5:325.

In certain embodiments, the combination of naltrexone and acetaminophen is administered once, twice, three, or four times per day.

The term "pain" refers to a discomfort caused by intense or damaging stimuli including illness, injury, or mental anguish.

The term "emotional pain" refers to trauma pain of a psychological, non-physical origin. In certain embodiments, emotional pain results from certain beliefs, thoughts, feelings or behaviors. In certain embodiments, emotional pain includes a subjective experience that involves awareness of negative changes in the self and its functions that is accompanied by negative feelings. Examples of mental ailments that can cause emotional pain include a pathology consisting of adjustment disorder.

The term "adjustment disorder" refers to states of subjective distress and emotional disturbance, usually interfering with social functioning and performance, arising in the period of adaptation to a significant life change or a stressful life event. The stressor may have affected the integrity of an individual's social network (bereavement, separation experiences). An example of adjustment disorder is emotional disturbance. Non-limiting examples of symptoms of emotional disturbance include feelings of abandonment, ambivalence, anger, anguish, anxiety, betrayal, compulsion, confusion, despair, deterioration, emptiness, failure, fatigue, fear, frustration, grief, guilt, helplessness, hopelessness, horror, hurt feelings, inferiority, insomnia, irritation, loneliness, loss of meaning, lure of death, powerlessness, rejection, sadness, self-hate, shame, stress, terror, ruminations, and worthlessness. Three adjustment disorder diagnosis codes are in the top seven most frequently used codes by therapists, psychologists, social workers, and counselors. (ICD-10 version: 2016, This disorder is referred to as code-F43.20. in particular: adjustment disorder with depressed mood (F43.21), adjustment disorder with anxiety (F43.22), adjustment disorder with mixed anxiety and depressed mood (F43.23), adjustment disorder with disturbance of conduct (F43.24), adjustment disorder with mixed disturbance of emotions and conduct (F43.25), and adjustment disorder with other symptoms (F43.29), in the International Statistical Classification of Diseases and Related Health Problems, $10^{th}$ Edition (2016) ("ICD-10 version: 2016"), the relevant portions of which are incorporated herein by reference in their entireties.

The term "physical pain" refers to pain felt in the body. While physical pain can accompany emotional pain, the two types of pain are distinct. In certain embodiments, physical pain includes a differentiated pain that is localized in the body and is often associated with noxious physical stimuli. Non-limiting examples of physical pain include neuropathic pain, nociceptive pain, and nociceptive pain with an allodynic component, migraine, inflammation, osteoarthritis, rheumatoid arthritis, psoriatic arthritis, trigeminal neuralgia, vulvodynia, irritable bowel syndrome, post herpetic neuralgia and diabetic neuropathy. Other examples of physical pain involve headache, migraine headache, back pain, lower back pain inflammation, osteoarthritis, rheumatoid arthritis, psoriatic arthritis, trigeminal neuralgia, vulvodynia, irritable bowel syndrome, post herpetic neuralgia, and diabetic neuropathy.

In certain embodiments, a subject experiencing physical pain is treated with a combination of acetaminophen and an opioid TLR4 antagonist. In certain embodiments, acetaminophen is administered in combination with an opioid TLR4 antagonist selected from naltrexone, norbinaltorphimine, nalmefene, naloxone, nalorphine, methylnaltrexone, samidorphan, cyprodime, naltrindole, amentoflavone, naltriben, norbinaltorphimine, 6-β-naltrexol, metabolites and pro drugs thereof, or pharmaceutically acceptable salts or solvates of any thereof. In certain embodiments, the opioid TLR4 antagonist is naltrexone. In other embodiments, the naltrexone is (+)-naltrexone (dextro-naltrexone).

In certain embodiments, the naltrexone, or a pharmaceutically acceptable salt or solvate thereof, is administered to the mammal at about 1.5 mg per day, and the acetaminophen, or a pharmaceutically acceptable salt or solvate thereof, is administered to the mammal at about 325 mg per day. In certain embodiments, the naltrexone, or a pharmaceutically acceptable salt or solvate thereof, is administered to the mammal at about 3.25 mg per day, and the acetaminophen, or a pharmaceutically acceptable salt or solvate thereof, is administered to the mammal at about 325 mg per day.

In certain embodiments, emotional pain is pain that is not physical pain and physical pain is pain that is not emotional pain. While, subjects can experience both simultaneously, these two types of pain are distinct. Physical pain can cause emotional pain. For instance, a subject suffering from a migraine may also experience sadness or anger from activities that the migraine headache is preventing the subject from doing. Emotional pain can also cause physical pain, for example, someone who is suffering self-hate may engage in physical self-harm.

In certain embodiments, the subject is experiencing only emotional pain. In other embodiments, the subject is experiencing emotional and physical pain.

In certain embodiments, the subject is experiencing emotional pain and low back pain. In other embodiments, the subject is experiencing emotional pain and migraine. In other embodiments, the subject is experiencing emotional pain and insomnia. In certain embodiments, the subject is experiencing low back pain and insomnia. In other embodiments, the subject is experiencing migraine and insomnia.

In certain embodiments, the subject is experiencing emotional pain and drug abuse or drug addiction. In other embodiments, the subject is experiencing emotional pain and alcohol abuse or alcohol addiction. In other embodiments, the subject experiencing emotional pain is not experiencing drug abuse or drug addiction. In other embodiments, the subject experiencing emotional pain is not experiencing alcohol abuse or alcohol addiction. In other embodiments, the subject experiencing emotional pain is neither experiencing drug abuse or drug addiction, nor alcohol abuse or alcohol addiction.

In certain embodiments, the subject is not suffering from drug abuse or addiction. According to some embodiments, the drug is alcohol or an opiate. According to specific embodiments, the opiate is selected from opium, morphine, codeine, oxycodone or heroin. In certain embodiments, the subject is suffering from drug abuse or addiction, but their pain does not originate from the abuse or addiction. The pain can be physical or emotional.

In certain embodiments, when the subject is experiencing both emotional and physical pain, the subject experiences a relief of symptoms in both emotional and physical pain following treatment with naltrexone or naltrexone and acetaminophen. In other embodiments, the subject only experiences a relief in symptoms from physical or emotional pain following treatment with naltrexone or naltrexone and acetaminophen. In other embodiments, the subject experiences similar extent of relief in both emotional and physical pain following treatment with naltrexone or naltrexone and acetaminophen. In other embodiments, the subject experiences more relief in emotional or physical pain following treatment with naltrexone or naltrexone and acetaminophen.

In certain embodiments, the subject experiencing a relief in pain experiences a dulling or blunting of emotions following treatment with naltrexone or naltrexone and acetaminophen. In certain embodiments, the subject experiencing a relief in pain is unable to experience pleasure (i.e., "anhedonic"), following treatment with naltrexone or naltrexone and acetaminophen. In other embodiments, the subject experiencing a relief in pain does not experience a blunting or dulling of emotions following treatment with naltrexone or naltrexone and acetaminophen.

In certain embodiments, the disclosure provides a method of inducing anhedonia in a subject suffering from pain. In some specific embodiments, the induction of anhedonia includes the reduction of intensity of emotion either positive or negative to a perceptible degree. In some embodiments, the pain is emotional pain. In other embodiments, the pain is physical pain. In certain embodiments, the subject is not suffering from substance abuse or addiction or their pain is not a result of substance abuse or addiction.

In certain embodiments, the subject is a mammal. In certain embodiments, the mammal is selected from rodents, primates, dogs, cats, camelids and ungulates. The term "rodent" refers to any species that is a member of the order rodentia including mice, rats, hamsters, gerbils and rabbits. The term "primate" refers to any species that is a member of the order primates, including monkeys, apes, and humans. The term "camelids" refers to any species that is a member of the family camelidae including camels and llamas. The term "ungulates" refers to any species that is a member of the superorder ungulata including cattle, horses and camelids. According to some embodiments, the mammal is a human.

Pharmaceutical Compositions

In certain embodiments, the combination of acetaminophen and opioid TLR4 antagonist is formulated with a pharmaceutically acceptable carrier. The pharmaceutical compositions and formulations can be administered orally, parenterally, topically, rectally, or by local administration, such as by aerosol or trans-dermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., Remington: The Science and Practice of Pharmacy, 21st ed., 2005.

The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Pharmaceutical formulations of the invention can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc., and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragées, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragée cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers adjusted for osmolarity.

In certain embodiments, the pharmaceutical compositions and formulations are parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or di-glycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid biochem. Mol. Biol. 58:611-617; Groning (1996) Pharmazie 51:337-341; Fotherby (1996) Contraception 54:59-69; Johnson (1995) J. Pharm. Sci. 84: 1 144-1 146; Rohatagi (1995) Pharmazie 50:610-613; Brophy (1983) Eur. J. Clin. Pharmacol. 24: 103-108; Remington: The Science and Practice of Pharmacy, 21st ed., 2005). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate. Single or multiple administrations of formulations can be given depending on for example: the dosage and frequency as required and tolerated by the patient, the degree and amount of cholesterol homeostasis generated after each administration, and the like. The formulations should provide a sufficient quantity of active agent to effectively treat, prevent or ameliorate conditions, diseases or symptoms, e.g., treat emotional pain.

EXAMPLES

The examples disclosed in the instant application are case studies from clinical trials. These examples are non-limiting and are merely representative.

Example 1: Naltrexone/Acetaminophen Open-Label Study for Treatment of Low Back Pain (with Evaluation of Coexisting Emotional Pain)

Twenty patients of whom 16 had chronic low back pain (CLBP), three had acute LBP and one had pain due to Temporomandibular disorders (TMD) were evaluated in an open label pilot study. After a baseline period evaluation, treatment was initiated with acetaminophen or naltrexone/acetaminophen. The patients on naltrexone alone (N=8), were treated for 9.83 days on average and patients treated with naltrexone/acetaminophen (N=18) were treated for a period of 25.4 on average. The patients completed daily diary evaluations in pre-treatment, after the first dose (average 7.39 hours) and while on-treatment (the score of the last day of treatment was recorded). The patient reported diary questionnaire included the following questions.

Question No. 1: Choose one number that best describes the "Worst Pain" in your lower back in the last 24 hours (WPI) [measured on an 11-point NRS (0=no pain, 10=worst pain possible)].

Question No. 2: Choose one number that best describes the "Average Pain" in your lower back in the last 24 hours (API) [measured on an 11-point NRS (0=no pain, 10=worst pain possible)].

Question No. 3: Choose one number that best describes the "Worst Emotional Pain" you experienced in the last 24 hours. (E.g., "Today, I experienced hurt feelings, and/or anger, and/or fear, and/or sadness").

Question No. 4: Choose one number that best describes how pain has interfered with your sleep in the last 24 hours [Pain Related Sleep Interference (PRSI) measured on an 11-point NRS (0=no interference, 10=complete interference)].

Question No. 5: Have you experienced difficulty sleeping or falling asleep (insomnia) in the last 24 hours [measured on an 11-point NRS (0=no insomnia, 10=worst insomnia possible)].

Question No. 6: How much change has the study medication provided in the last 24 hours compared to before starting the study medication regarding the overall condition [measured on a seven-point bipolar (Likert) scale (1=very much worse; 2=much worse; 3=minimally worse; 4=no change; 5=minimally improved; 6=much improved; and 7=very much improved)].

Question No. 7: How much change has the study medication provided in the last 24 hours compared to before starting the study medication regarding your energy level [measured on a seven-point bipolar (Likert) scale (1=very much worse; 2=much worse; 3=minimally worse; 4=no change; 5=minimally improved; 6=much improved; and 7=very much improved)].

Question No. 8: How much change has the study medication provided in the last 24 hours compared to before starting the study medication regarding your activity level [measured on a seven-point bipolar (Likert) scale (1=very much worse; 2=much worse; 3=minimally worse; 4=no change; 5=minimally improved; 6=much improved; and 7=very much improved)].

Question No. 9: The number of doses of the medication consumed.

TABLE 1

Data and Post-Treatment Improvement with acetaminophen Alone and with Naltrexone/acetaminophen

| | | WPI Avg. (SD) | API Avg. (SD) | WEP Avg. (SD) | PRSI Avg. (SD) | Insomnia Avg. (SD) | PGIC Avg. (SD) | Energy Avg. (SD) | Activity Avg. (SD) | Doses Taken Avg. (SD) |
|---|---|---|---|---|---|---|---|---|---|---|
| Baseline (N = 21) | | 6.68 (1.85) | 5.53 (2.08) | 5.45 (2.58) | 4.90 (3.32) | 4.10 (3.37) | | | | |
| Treatment with APAP 325 mg alone (N = 8), Average days in treatment (SD): 9.83 (9.79) | | 5.25 (2.32) | 4.25 (2.12) | 5.17 (2.80) | 4.00 (2.88) | 4.33 (4.13) | 5.00 (0.00) | 4.67 (0.52) | 4.67 (0.52) | 4.83 (2.04) |
| after 1rst dose treatment with NTX/APAP 2.25/325 mg (n = 12), Hours after 1rst dose, Average (SD): 7.39 (9.49) | | 3.29 (2.03) | 2.88 (1.55) | 2.08 (1.87) | | | 6.78 (0.44) | 5.56 (1.33) | 6.11 (1.27) | 2.00 (1.63) |
| Treatment with NTX/APAP 2.25/325 mg (n = 18) Avg. (SD): 25.4 (38.47) | | 1.22 (1.26) | 0.56 (0.95) | 1.11 (1.71) | 0.03 (0.12) | 0.03 (0.12) | 6.84 (0.37) | 5.74 (1.28) | 6.16 (1.01) | 3.41 (0.94) |
| Mean Improvement from Baseline | APAP alone | 1.43 | 1.28 | 0.14 | 0.90 | −0.23 | | | | |
| | NTX/APAP Post 1st dose | 3.39 | 2.65 | 3.23 | 4.50 | 2.70 | | | | |
| | NTX/APAP Treatment Period | 5.46 | 4.97 | 4.34 | 4.87 | 4.07 | | | | |
| p-value APAP alone vs. NTX/APAP | After treatment | 0.0001 | 0.0001 | 0.0001 | <0.0001 | 0.0001 | | | | |

APAP = acetaminophen
WPI = Worst Pain Intensity; patient reported 24-hour WPI was measured on 11-point NRS, (0 = no pain, 10 = worst imaginable pain)
API = average pain intensity; patient reported 24-hour API was measured on 11-point NRS, (0 = no pain, 10 = worst imaginable pain)
WEP = Worst Emotional Pain; patient reported 24-hour WEP was measured on 11-point NRS, (0 = no emotional pain, 10 = worst emotional pain imaginable)
PRSI = Pain Related Sleep Interference; patient reported 24-hour PRSI was measured on 11-point NRS, (0 = no interference, 10 = complete interference)
Insomnia = difficulty sleeping or falling asleep; patient reported 24-hour Insomnia was measured on 11-point NRS, (0 = no insomnia, 10 = worst imaginable insomnia)
PGIC = Patient Global Impression of Change; 24-hour PGIC was measured on a seven-point bipolar (Likert) scale (1 = very much worse; 2 = much worse; 3 = minimally worse; 4 = no change; 5 = minimally improved; 6 = much improved; and 7 = very much improved)
p-value by Comparison of means After a baseline period evaluation, eight patients were treated first with acetaminophen alone for an average period of 9.83 days, (standard deviation (SD)—9.79) and then with naltrexone/acetaminophen 2.25 mg/325 mg for an average period of 25.4 days, (SD—38.47). The post first dose evaluation occurred on average 7.39, (SD—9.49) hours after the first dose was taken. The results are presented in the Tables above. The study demonstrated mean Worst Pain Intensity (WPI) improvement from baseline of 5.46, average pain intensity (API) improvement of 4.97, the mean Worst Emotional Pain (WEP) improvement was 4.34, and Insomnia improvement was 4.07 on (0-10 NRS). Patient Global Impression of Change (PGIC) was 6.84 (much improved=6, and very much improved=7). Patients who were treated with acetaminophen alone had a mean improvement in WPI of 1.43, API improvement of 1.28, WEP improvement was 0.14, and insomnia improvement of −0.23. The improvement of patients treated with naltrexone/acetaminophen was much higher than that of patients who were treated with acetaminophen alone. The pilot study with NTX/acetaminophen 2.25 mg/325 mg for LBP demonstrated significant improvement in pain intensity, emotional pain, and insomnia.

In conclusion, in the LBP pilot study, P-value for naltrexone/acetaminophen vs. acetaminophen alone was 0.0001 for each of the following: WPI, API, WEP, PRSI, and insomnia. These findings demonstrated synergism of naltrexone/acetaminophen compared to its individual component, acetaminophen, for physical pain, emotional pain, and insomnia.

Naltrexone/Clonidine IND Phase II Clinical Trial in CLBP

Additionally, a phase II IND clinical trial found that a naltrexone/clonidine combination (ANC05) was effective for treatment of neuropathic CLBP, compared to placebo. In this study, seventy-eight subjects with neuropathic chronic back pain diagnosis (in the lumbar or cervical region), supported by imaging abnormalities, were selected. The trial had a one-week Baseline Period, a three-week, double-blind, placebo-controlled Treatment Period, a 3-day Tapering Period and an open-label extension phase for non-responders (<30% improvement) following the same double-blind phase protocol. The primary outcome measure of the trial was the change from baseline to treatment Week 3 in the 24-hour Average Pain Intensity (API) measure on the 11-point numerical rating scale (NRS). Table 3 shows the API by day over the three-week Treatment Period. As shown in Table 2, subjects reported a mean 3.7-point improvement, compared to a 0.9-point improvement in the placebo subjects. The naltrexone/acetaminophen combination is more effective than naltrexone/clonidine, with a 5.29 average pain intensity improvement, as shown above.

TABLE 2

Phase II IND Trial-Change from Baseline to Week 3 in Average Pain Intensity

Mean Average Pain Intensity-Week-3

| | | N | Baseline | Wk3 | Change (SE) | p-value | Groups Method | groups in DB t-Test, 2-sided |
|---|---|---|---|---|---|---|---|---|
| BOCF | Placebo | 34 | 5.50 | 4.59 | −0.91 (0.36) | 0.00000 | P Value Mean Difference | <0.00001 −2.78 |
| BOCF | ATNC05 | 44 | 5.55 | 1.86 | −3.69 (0.34) | | Standard Error 99% Confidence Interval | ±0.35 (−4.131 to −1.429) |

Example 2: Emotional Pain Due to Adjustment Disorder Due to Grieving Passing of a Pet A 56-year-old female flight attendant who has been in a long term relationship with a man, had to euthanize her cat the day before she was seen. She had a history of depression, which has been under control on treatment with two antidepressant medications and xanax (a commonly used benzodiazepine tranquilizer).

She has been upset for the preceding two months due to her cat's cancer diagnosis. In spite of having modest financial means she paid for chemotherapy and radiation treatments. Subsequently, she accepted the veterinarian's advice to euthanize the cat.

During the clinic visit, the patient cried uncontrollably. She stated: "I cry all the time, I have no interest in interacting with my boyfriend or his daughters who are trying to console me, I feel guilty all the time for not doing more to save the cat, I feel the future is hopeless, I don't have any reason to live anymore". She stated that xanax was not helping her this time.

The patient experienced a stressful life event (bereavement) that interfered with her social functioning. The patient was diagnosed with adjustment disorder (ICD-10, F43.20). The most common available treatment for this condition, is a benzodiazepine, but since the patient reported that xanax did not help her this time, she agreed to be treated with naltrexone/acetaminophen. She took naltrexone/acetaminophen 2.25 mg/325 mg every 12 hours for 9 days. She completed emotional pain diary assessments daily after the morning dose at specific time points. The emotional pain intensity was rated on a 4-point unipolar scale (0=none, 1=mild, 2=moderate, 3=severe). The patient specified that her emotional pain is due to emotional disturbance from hurt feelings, sadness, and fear, she did not experience anger.

The patient received the first dose of naltrexone/acetaminophen 2.25 mg/325 mg in the clinic, she rated her pre-dose emotional pain intensity as severe (grade 3), at 7-minutes after dosing, her emotional pain was moderate (grade 2), and at 30 minutes it was mild (grade 1). The patient continued to take naltrexone/acetaminophen 2.25 mg/325 mg twice daily for 9 days.

There was a highly statistically significant improvement from baseline at 1, 2, 3, 4, 6, and 12 hours post dose (p-values, 0.0087, 0.0087, 0.0003, 0.0001, 0.0007, <0.0001 respectively) in emotional pain, in addition, after the first dose the patient reported emotional pain relief as early as 7 minutes and 30 minutes.

On three return visits, the patient stated that naltrexone/acetaminophen 2.25 mg/325 mg helped her get through the rough patch, it helped lessening her guilt feelings, but it did not make her lack empathy. After 9 days of treatment, her emotional pain became mild, at that time she elected to stop the treatment. 5 days later, she reports her emotional pain as moderate (off treatment).

This case study demonstrated naltrexone/acetaminophen 2.25 mg/325 administered BID significantly improved symptoms of adjustment disorder due to grieving during the most distressful 9 days immediately the loss of a pet. Naltrexone/acetaminophen 2.25 mg/325 offered relief where a benzodiazepine tranquilizer did not work.

TABLE 3

Emotional Pain Due to Grief for Loss of Person's Pet Cat

| Date | Dose time | Before dose | 7 min | 30 min | 1 h | 2 h | 3 h | 4 h | 6 h | 12 h |
|---|---|---|---|---|---|---|---|---|---|---|
| Oct. 12, 2016 | 3:30 p.m. | 3 | 2 | 1 | 1 | 1 | 1 | 2 | 3 | |
| Oct. 13, 2016 | 9:30 a.m. | 3 | | | | | | | 1 | |
| Oct. 14, 2016 | 9:30 a.m. | 3 | | | | | | | 2 | |
| Oct. 15, 2016 | 9:30 a.m. | 3 | 3 | 3 | 3 | 3 | 2 | 2 | 2 | 2 |
| Oct. 16, 2016 | 9:30 a.m. | 2 | 2 | 2 | 2 | 2 | 1 | 1 | 1 | 1 |
| Oct. 17, 2016 | 9:30 a.m. | 3 | 3 | 3 | 2 | 2 | 2 | 1 | 1 | 1 |
| Oct. 18, 2016 | 9:30 a.m. | 3 | 3 | 3 | 2 | 2 | 2 | 1 | 1 | 1 |
| Oct. 19, 2016 | 9:30 a.m. | 2 | 2 | 2 | 1 | 1 | 1 | 1 | 1 | 1 |
| Oct. 20, 2016 | 9:30 a.m. | 2 | 2 | 2 | 1 | 1 | 1 | 1 | 1 | 1 |

TABLE 3-continued

Emotional Pain Due to Grief for Loss of Person's Pet Cat

| Date | Dose time | Before dose | 7 min | 30 min | 1 h | 2 h | 3 h | 4 h | 6 h | 12 h |
|---|---|---|---|---|---|---|---|---|---|---|
| | Average | 2.67 | 2.43 | 2.29 | 1.71 | 1.71 | 1.43 | 1.29 | 1.44 | 1.17 |
| | Standard deviation | 0.50 | 0.53 | 0.76 | 0.76 | 0.76 | 0.53 | 0.49 | 0.73 | 0.41 |
| | P-value vs. pre-morning dose | | | 0.2475 | 0.0087 | 0.0087 | 0.0003 | 0.0001 | 0.0007 | <.0001 |

Example 3: Emotional Pain Due to Anger Towards Husband for Having an Affair

A 63-year-old female retired postal worker reported a long history of low back pain and depression. She also reported emotional pain due to anger towards her husband for conducting an extra-marital affair.

When the patient discovered that her husband was having an affair, she became upset and over a one-year period lost 100 pounds in body weight. The affair ended two years before the study, and the couple stayed together. However, the patient carried constant anger towards her husband. She reported that once, prior to the study, she had an urge to hurt him while he was asleep. The patient requested that her antidepressant dose be increased since it wasn't controlling her emotional disturbance, (however, she has been already on the maximal allowable dose of the antidepressant). The patient reported a poor night's sleep the night before.

The patient was diagnosed with adjustment disorder (ICD-10, F43.20) since she exhibited maladaptive response to a stressful life event. Available treatments can include treatment with an antidepressant, however, since she reported that her antidepressant was not helping, she was offered naltrexone/acetaminophen. The patient was treated with naltrexone 2.25 mg twice daily and acetaminophen 325 mg twice daily. After the first dose, the patient reported being sleepy, and feeling calm and peaceful during the whole day. She slept most of the day and slept well at night. The next day the patient reported not saying anything negative to her husband, which was unusual for her. In addition to improvement in emotional pain she also had improvement in the physical pain in her low back.

Table 43 illustrates the decrease in emotional and physical pain after treatment with naltrexone and acetaminophen. Worst emotional pain, pain related sleep interference, and insomnia were eliminated after treatment, and the average pain intensity (API) decreased by 57% after treatment.

TABLE 4

Emotional pain due to anger towards husband for conducting an affair

| Medication | Date start | Date end | WPI | API | WEP | PRSI | Insomnia | PGIC |
|---|---|---|---|---|---|---|---|---|
| None-pre dose | Oct. 5, 2015 | Oct. 5, 2015 | 7 | 7 | 6 | 6 | 8 | |
| Naltrexone 2.25 mg/ acetaminophen 325 mg B.I.D. | Oct. 6, 2015 | Oct. 6, 2015 | 5 | 3 | 0 | 0 | 0 | 7 |
| Change from baseline | | | 29% | 57% | 100% | 100% | 100% | | acetaminophen = acetaminophen

WPI = Worst Pain Intensity; patient reported 24-hour WPI was measured on 11-point NRS, (0 = no pain, 10 = worst possible pain)

API = average pain intensity; patient reported 24-hour API was measured on 11-point NRS, (0 = no pain, 10 = worst possible pain)

WEP = Worst Emotional Pain; patient reported 24-hour WEP was measured on 11-point NRS, (0 = no emotional pain, 10 = worst emotional pain possible)

PRSI = Pain Related Sleep Interference; patient reported 24-hour PRSI was measured on 11-point NRS, (0 = no interference, 10 = complete interference)

Insomnia = difficulty sleeping or falling asleep; patient reported 24-hour Insomnia was measured on 11-point NRS, (0 = no insomnia, 10 = worst possible insomnia)

B.I.D. = two times a day

PGIC = Patient Global Impression of Change; 24-hour PGIC was measured on a seven-point bipolar (Likert) scale (1 = very much worse; 2 = much worse; 3 = minimally worse; 4 = no change; 5 = minimally improved; 6 = much improved; and 7 = very much improved)

Example 4: Emotional Pain Due to Adjustment Disorder Due to Football Team Losses A 51-year-old female office manager was a life-long Miami Dolphin's football team fan who reported becoming upset when the Dolphins played badly or lost. She stated that the teams loses, she cannot not put it out of her mind couple of days.

The patient had a history of low back pain, for which she took Tylenol 325 mg, 4 times daily for 10 days. During that time, she did not report improvement in her ability to handle her emotional disturbance due to the team losses.

It is well known that sports fan are emotionally invested in their team's performance, the long string of bad play and losses, presented a stressful life event for her, she was diagnosed with adjustment disorder (ICD-10, F43.20). She agreed to take naltrexone/acetaminophen since she was not willing to take a benzodiazepine tranquilizer.

She was placed on naltrexone 2.25 mg twice a day together with acetaminophen 325 mg twice a day for a one month period, during that time, the Miami Dolphins played badly. During this time the patient reported feeling disappointment when the Dolphins lost, the loss did not bother her after the game ended.

Table 5 illustrates 100% elimination of emotional and physical pain after treatment with naltrexone and acetaminophen for one month, while acetaminophen alone reduced those symptoms by 25%-40%.

This case study demonstrated naltrexone/acetaminophen 2.25 mg/325 significantly improved symptoms of adjustment disorder due to emotional disturbance from feelings of anger caused by losses of a person's sports team.

TABLE 5

Emotional pain due to anger caused by a team's loss of a football game

| Medication | Date start | Date end | WPI | API | WEP | PRSI | Insomnia |
| --- | --- | --- | --- | --- | --- | --- | --- |
| None | Jun. 28, 2015 | Jun. 28, 2015 | 5 | 4 | 3 | 0 | 0 |
| APAP 325 mg Q.I.D. | Jun. 29, 2015 | Jul. 8, 2015 | 3 | 3 | 2 | 0 | 0 |
| NTX 2.25 mg/APAP 325 mg Q.I.D. | Jul. 9, 2015 | Aug. 9, 2015 | 0 | 0 | 0 | 0 | 0 |
| Improvement from baseline for APAP | | | 40% | 25% | 33% | | |
| Improvement from baseline for NTX/APAP | | | 100% | 100% | 100% | | |

NTX = naltrexone

APAP = acetaminophen

WPI = Worst Pain Intensity; patient reported 24-hour WPI was measured on 11-point NRS, (0 = no pain, 10 = worst possible pain)

API = average pain intensity; patient reported 24-hour API was measured on 11-point NRS, (0 = no pain, 10 = worst possible pain)

WEP = Worst Emotional Pain; patient reported 24-hour WEP was measured on 11-point NRS, (0 = no emotional pain, 10 = worst emotional pain possible)

PRSI = Pain Related Sleep Interference; patient reported 24-hour PRSI was measured on 11-point NRS, (0 = no interference, 10 = complete interference)

Insomnia = difficulty sleeping or falling asleep; patient reported 24-hour Insomnia was measured on 11-point NRS, (0 = no insomnia, 10 = worst possible insomnia)

Q.I.D. = four times a day

PGIC = Patient Global Impression of Change; 24-hour PGIC was measured on a seven-point bipolar (Likert) scale (1 = very much worse; 2 = much worse; 3 = minimally worse; 4 = no change; 5 = minimally improved; 6 = much improved; and 7 = very much improved)

Example 5: Emotional Pain Due to Due Adjustment Disorder Due to Fear from Exposure to a Near Airplane Crash A 44-year-old female flight attendant reported chronic low back pain, and tendinitis of the left foot. Prior to this study, she had used acetaminophen and ibuprofen without significant relief. She was placed on naltrexone 2.25 mg and acetaminophen 325 mg Q.I.D her physical pains. While on treatment with naltrexone/acetaminophen for her physical pains, the patient experienced a stressful life event, a Miami-Frankfurt flight she was working on had a mechanical problem. The captain declared an emergency and landed at the nearest airport in Halifax, Canada. The patient reported that other crew members displayed a great deal of distress knowing that they could have died if the flight had continued over the Atlantic Ocean. In contrast, the patient felt very much in control, she felt calm and had no extreme feelings. The pain in her low back and foot was much better too.

Example 6: Emotional Pain Due to Adjustment Disorder Due to Severe Pain Caused by Acute Spinal Disk Herniation A 39-year-old male restaurant waiter reported a sudden onset of severe lower back pain with radiation to his left leg. He scheduled an elective inguinal hernia surgery during a time that he had already planned time off from work for his wife and himself. On the 11-point numerical rating scale (NRS) (0=no pain, 10=worst pain possible), the patient reported that his worst pain level was 10/10, and his average pain level was 9/10. He reported an emotional pain level of 6/10, due to the physical pain and the uncertainty regarding the need to cancel his scheduled plans. His pain related sleep interference (PRSI) was 10/10 and insomnia was 10/10. The day after the incident, he took acetaminophen 3000 mg. His pain level and insomnia improved by 1 point, his emotional pain remained a 6/10. The following day, he was placed on naltrexone 2.25 mg and acetaminophen 325 mg Q.I.D. For the next three days his average pain declined to 4/10; his worst pain declined to 5/10; and his emotional pain, PRSI, and insomnia were 0/10. He was able to undergo the planned elective surgery. Sometime after the surgery, his pain level was 0/10; however, he rated his emotional pain as 6/10 and his insomnia 7/10. He was in the process of purchasing a home, which he found stressful. He stated that while he was on naltrexone/acetaminophen he felt calm.

Table 6 demonstrates the improvement in the patient's physical and emotional pain after treatment with naltrexone/acetaminophen.

This case study demonstrated naltrexone/acetaminophen 2.25 mg/325 administered QID treated adjustment disorder due to feelings of inability to cope or plan ahead due to unexpected severe illness.

TABLE 6

Emotional pain due to severe pain caused by herniated disk

| Medication | Date start | Date end | WPI | API | WEP | PRSI | Insomnia | PGIC |
|---|---|---|---|---|---|---|---|---|
| None | Aug. 17, 2015 | Aug. 17, 2015 | 10 | 9 | 6 | 10 | 10 | |
| APAP 1000 mg TID | Aug. 18, 2015 | Aug. 19, 2015 | 9 | 8 | 6 | 9 | 9 | 5 |
| Naltrexone 2.25 mg/APAP 325 mg Q.I.D. | Aug. 19, 2015 | Aug. 20, 2015 | 6 | 5 | 3 | 0 | 0 | 7 |
| Naltrexone 2.25 mg/APAP 325 mg Q.I.D. | Aug. 21, 2015 | Aug. 21, 2015 | 5.5 | 4.5 | 0 | 0 | 0 | 7 |
| Naltrexone 2.25 mg/APAP 325 mg Q.I.D. | Aug. 22, 2015 | Aug. 22, 2015 | 5 | 4 | 0 | 0 | 0 | 7 |
| Naltrexone 2.25 mg/APAP 325 mg Q.I.D. | Aug. 23, 2015 | Aug. 23, 2015 | 4.5 | 3.5 | 0 | 0 | 0 | 7 |
| Naltrexone 2.25 mg/APAP 325 mg Q.I.D. | Sep. 30, 2015 | Sep. 30, 2015 | 0 | 0 | 6 | 0 | 7 | 7 |

APAP = acetaminophen

WPI = Worst Pain Intensity; patient reported 24-hour WPI was measured on 11-point NRS, (0 = no pain, 10 = worst possible pain)

API = average pain intensity; patient reported 24-hour API was measured on 11-point NRS, (0 = no pain, 10 = worst possible pain)

WEP = Worst Emotional Pain; patient reported 24-hour WEP was measured on 11-point NRS, (0 = no emotional pain, 10 = worst emotional pain possible)

PRSI = Pain Related Sleep Interference; patient reported 24-hour PRSI was measured on 11-point NRS, (0 = no interference, 10 = complete interference)

Insomnia = difficulty sleeping or falling asleep; patient reported 24-hour Insomnia was measured on 11-point NRS, (0 = no insomnia, 10 = worst possible insomnia)

Q.I.D. = four times a day

T.I.D. = three times daily

PGIC = Patient Global Impression of Change; 24-hour PGIC was measured on a seven-point bipolar (Likert) scale (1 = very much worse; 2 = much worse; 3 = minimally worse; 4 = no change; 5 = minimally improved; 6 = much improved; and 7 = very much improved)

Example 7: Emotional Pain Due to Adjustment Disorder Due to Conflict at Work A 51-year-old male, a U.S. Postal mail processor, and union representative in a Main Processing Facility had a 15-year history of lower back pain. He also reported experiencing emotional pain due to his function as a union representative who handled irate co-workers.

His baseline average pain level was 4.5/10, and his worst pain was 5/10 on the 11-point NRS. One day, after taking acetaminophen 4 times, he reported slight improvement in his back pain, but did not notice a change in emotional pain.

The patient was placed on naltrexone 2.25 mg and Tylenol 325 mg twice daily. Within three days his back pain resolved completely. He also reported that he handled emotional pain a lot better. He was able to stay calm and deal with co-workers' emotions rationally, and he was not affected by their emotional states as he was before. He noticed that he resolved conflicts more effectively than before and did not dwell on their problems. He was more tolerant and did not experience less joy. The patient also stated that he slept longer hours and felt rested during the day.

This case study demonstrated naltrexone/acetaminophen 2.25 mg/325 administered BID treated adjustment disorder due to stressful life event at work.

Example 8: Emotional Pain Due to Adjustment Disorder Due to Anger with Wife

An 87-year-old retired male chef had a two-year history of post herpetic neuralgia (PHN) and a long history of chronic lower back pain. He was treated for PHN with naltrexone 5 mg and clonidine 0.025 mg twice daily for six months. Then he was switched to naltrexone 5 mg twice daily for 6 months. He was then switched to naltrexone 2.25 mg four times and acetaminophen 325 mg four times daily. While on naltrexone 5 mg/clonidine and naltrexone alone, his mean average pain intensity went down to 1.5/10. When he was on naltrexone/acetaminophen his mean average pain intensity went down to 0.25/10.

While he was on naltrexone alone, the patient reported an incident when he was upset with his wife and his anger led him to throw his car key forcefully to the ground, causing it to break. However, after being on naltrexone and acetaminophen, he and his wife report that he was calmer than before.

This case study demonstrated naltrexone/acetaminophen 2.25 mg/325 administered BID treated adjustment disorder due to emotional disturbance due to feelings of anger.

Example 9: Emotional Pain Due to Adjustment Disorder Due to Anger with Husband A 74-year-old female homemaker had a long history of chronic migraines and lower back pain. She also experienced emotional pain that arose from anger towards her husband.

For 30 years she and her retired husband were always together. During that time, she frequently criticized his actions. Prior to being treated, she estimated that she criticized him about three times an hour. The patient was placed on naltrexone 5 mg twice daily for chronic migraines and lower back pain. While on naltrexone for 14 months, she reported that she criticized her husband half as much, her migraine intensity and frequency were lessened by 90%, and her lower back pain diminished by 90%.

The patient was placed on naltrexone 2.25 mg and acetaminophen 325 mg four times daily. After two-and-a-half months of treatment, she reported that she did not get upset with her husband's actions and she criticized him only about once a day. Her husband agreed that in the past two-and-a-half months she criticized him only once a day and stated "we are good now."

This case study demonstrated naltrexone/acetaminophen 2.25 mg/325 administered BID treated adjustment disorder due to emotional disturbance due to feelings of anger.

Example 10: Emotional Pain Due to Adjustment Disorder Due to Anger with Poorly-Performing Employees A 39-year-old male building contractor with a history of lower back pain reported emotional pain due to frustration with his three employees' poor job performance. Treatment with acetaminophen for three days improved his back pain, but his emotional pain remained unchanged. Treatment with naltrexone and acetaminophen eliminated his physical, as well as his emotional pain, which happened overnight.

Table 7 illustrates the elimination of the patient's emotional pain and insomnia, and reduction of pain related sleep interference. Symptoms returned after treatment was discontinued.

This case study demonstrated naltrexone/acetaminophen 2.25 mg/325 administered BID treated adjustment disorder due to emotional disturbance due to feelings of anger.

TABLE 7

| Emotional pain due to anger with poorly-performing employees | | | | | | | | |
|---|---|---|---|---|---|---|---|---|
| Medication | Date start | Date end | WPI | API | WEP | PRSI | Insomnia | PGIC |
| None | Sep. 22, 2015 | Sep. 28, 2015 | 7 | 5 | 3 | 7 | 6 | |
| APAP 325 mg Q.I.D. | Sep. 29, 2015 | Oct. 1, 2015 | 4 | 2.5 | 3 | 4 | 2 | 5 |
| Naltrexone 2.25 mg/APAP 325 mg Q.I.D. | Oct. 2, 2015 | Oct. 2, 2015 | 0 | 0 | 0 | 0 | 4 | 7 |
| Naltrexone 2.25 mg/APAP 325 mg Q.I.D. | Oct. 3, 2015 | Oct. 3, 2015 | 1 | 0.5 | 0 | 1 | 0 | 7 |

TABLE 7-continued

Emotional pain due to anger with poorly-performing employees

| Medication | Date start | Date end | WPI | API | WEP | PRSI | Insomnia | PGIC |
|---|---|---|---|---|---|---|---|---|
| Discontinued Meds due to dizziness | Oct. 4, 2015 | Oct. 4, 2015 | 6 | 5 | 2 | 6 | 7 | 5 |

APAP = acetaminophen
WPI = Worst Pain Intensity; patient reported 24-hour WPI was measured on 11-point NRS, (0 = no pain, 10 = worst possible pain)
API = average pain intensity; patient reported 24-hour API was measured on 11-point NRS, (0 = no pain, 10 = worst possible pain)
WEP = Worst Emotional Pain; patient reported 24-hour WEP was measured on 11-point NRS, (0 = no emotional pain, 10 = worst emotional pain possible)
PRSI = Pain Related Sleep Interference; patient reported 24-hour PRSI was measured on 11-point NRS, (0 = no interference, 10 = complete interference)
Insomnia = difficulty sleeping or falling asleep; patient reported 24-hour Insomnia was measured on 11-point NRS, (0 = no insomnia, 10 = worst possible insomnia)
Q.I.D. = four times a day
T.I.D. = three times daily
PGIC = Patient Global Impression of Change; 24-hour PGIC was measured on a seven-point bipolar (Likert) scale (1 = very much worse; 2 = much worse; 3 = minimally worse; 4 = no change; 5 = minimally improved; 6 = much improved; and 7 = very much improved)

Example 11: Emotional Pain Due to a Adjustment Disorder Due to Relationship Break-Up A 59-year-old male retired flight attendant reported emotional distress due to being conflicted about breaking up with his partner. He lost 20 pounds over one month due to the emotional disturbance. He believed that he must end his 14-year relationship because of the partner's behavior, and experienced conflicted emotions, hurt feelings, and sadness.

Prior to treatment, the patient rated his emotional pain over the previous month a 10/10, (on the NRS). He was placed on acetaminophen 325 mg four times daily.

On the day of treatment, he was in severe emotional distress, on the verge of tears. He was given a single dose of naltrexone 2.25 mg and acetaminophen 325 mg. Thirty minutes later he stated that he could go home and talk about it rationally without crying. He stated that he felt calm, cool and collected. He stated that his sadness level decreased to 1/10. One hour after the dose, the patient reported that he had no emotional stress at all, and had no fear of the future. He stated that he was not sad, and that he felt great. He wanted to stay on the medication.

Table 8 illustrates the rapid improvement in the patient's emotional pain after administration of naltrexone/acetaminophen.

This case study demonstrated naltrexone/acetaminophen 2.25 mg/325 administered QID significantly improved symptoms of adjustment disorder due to loss of intimate relationship.

TABLE 8

Emotional pain due to a break-up

| Medication | Date start | Date end | WPI | API | WEP | PRSI | Insomnia | PGIC |
|---|---|---|---|---|---|---|---|---|
| None | Aug. 25, 2015 | Sep. 24, 2015 | 8 | 6 | 10 | 6 | 10 | |
| APAP 325 mg Q.I.D. | Sep. 25, 2015 | Oct. 2, 2015 | 7 | 5 | 10 | 3.5 | 10 | 5 |
| Naltrexone 2.25 mg/APAP 325 mg Q.I.D. single dose at 11:00 a.m. | Oct. 2, 2015 11:00 a.m. | Oct. 2, 2015 11:30 p.m. | 0* | 0* | 1* | | | 7 |
| | Oct. 2, 2015 11:00 am. | Oct. 2, 2015 12:00 p.m. | 0** | 0** | 0** | | | 7 |
| Naltrexone 2.25 mg/APAP 325 mg Q.I.D. | Oct. 3, 2015 | Oct. 5, 2015 | 2 | 0.5 | 5 | 0 | 0 | 7 |

APAP = acetaminophen
WPI = Worst Pain Intensity; patient reported 24-hour WPI was measured on 11-point NRS, (0 = no pain, 10 = worst possible pain)
API = average pain intensity; patient reported 24-hour API was measured on 11-point NRS, (0 = no pain, 10 = worst possible pain)
WEP = Worst Emotional Pain; patient reported 24-hour WEP was measured on 11-point NRS, (0 = no emotional pain, 10 = worst emotional pain possible)
PRSI = Pain Related Sleep Interference; patient reported 24-hour PRSI was measured on 11-point NRS, (0 = no interference, 10 = complete interference)
Insomnia = difficulty sleeping or falling asleep; patient reported 24-hour Insomnia was measured on 11-point NRS, (0 = no insomnia, 10 = worst possible insomnia)
Q.I.D. = four times a day
T.I.D. = three times daily
PGIC = Patient Global Impression of Change; 24-hour PGIC was measured on a seven-point bipolar (Likert) scale (1 = very much worse; 2 = much worse; 3 = minimally worse; 4 = no change; 5 = minimally improved; 6 = much improved; and 7 = very much improved)
*Change in the last half hour
**Change in the last one hour Example 12: Emotional Pain Due to Adjustment Disorder Due to Separation from a Child A 64-year-old female had been suffering from lower back pain and leg pain for 10 years. She also endured emotional pain due to separation from her son.

The patient was taking Naltrexone 2.25 mg four times daily and Clonidine 0.025 mg twice daily for five years. On that regimen, she reported that the back and leg pain decreased from an average of 5-5.5/10 to average of 3-4/10 on the NRS. During the five year period she reported that she felt emotionally hurt and sad because her son, an only child, who moved away from home when he was 17, was not calling her as frequently as she desired. When he called her, she always told him how hurt she was by his actions and that he needed him to call her more often.

The patient stopped the naltrexone/clonidine for 3 days. She then began taking acetaminophen 325 mg four times daily for 5 days. Following that, she took naltrexone alone for 12 days. While on naltrexone/clonidine, acetaminophen alone, and naltrexone alone she continued to report experiencing the same level of emotional pain due to the separation from her son.

For almost three months, the patient took naltrexone 2.25 mg four times daily and acetaminophen 325 mg four times daily. She reported that on that regimen she did not experience hurt or sadness over the separation from her son, and when he called she did not ask him to call more often nor did she mention her hurt feelings. She still felt love for him and wished to talk with him more often but she handled the separation better.

Table 9 illustrates the improvement in the patient's emotional pain with naltrexone/acetaminophen compared to ibuprofen, naltrexone/clonidine, naltrexone alone, or acetaminophen alone.

This case study demonstrated naltrexone/acetaminophen 2.25 mg/325 administered QID significantly improved symptoms of adjustment disorder due to separation from a loved one.

TABLE 9

Emotional pain due to separation from a child

| Medication | Date start | Date end | WPI | API | WEP | PRSI | Insomnia | PGIC |
|---|---|---|---|---|---|---|---|---|
| Ibuprofen 800 mg T.I.D. PRN | Feb. 1, 2006 | Apr. 9, 2010 | 6 | 5.5 | 7 | 7 | 9 | |
| Naltrexone 2.25 mg Q.I.D./Clonidine 0.025 mg Q.I.D. | Apr. 10, 2010 | Jun. 24, 2015 | 4 | 3.5 | 5.5 | 5.5 | 6 | 6 |
| None | Jun. 25, 2015 | Jun. 28, 2015 | 5 | 4.5 | 5.5 | 5 | 7 | 6 |
| APAP 325 mg Q.I.D. | Jun. 29, 2015 | Jul. 6, 2015 | 4.5 | 3.5 | 5.0 | 4.5 | 5.5 | 5 |
| Naltrexone 2.5 mg Q.I.D. | Jun. 27, 2015 | Jul. 8, 2015 | 5 | 4 | 5.5 | 5.5 | 6.5 | 6 |
| Naltrexone 2.25 mg/APAP 325 mg Q.I.D. | Jul. 9, 2015 | Oct. 4, 2015 | 1.5 | 0.5 | 0 | 0 | 0 | 7 |
| NTX/APAP % change vs. none | | | 70% | 89% | 100% | 100% | 100% | 100% |

APAP = acetaminophen

WPI = Worst Pain Intensity; patient reported 24-hour WPI was measured on 11-point NRS, (0 = no pain, 10 = worst possible pain)

API = average pain intensity; patient reported 24-hour API was measured on 11-point NRS, (0 = no pain, 10 = worst possible pain)

WEP = Worst Emotional Pain; patient reported 24-hour WEP was measured on 11-point NRS, (0 = no emotional pain, 10 = worst emotional pain possible)

PRSI = Pain Related Sleep Interference; patient reported 24-hour PRSI was measured on 11-point NRS, (0 = no interference, 10 = complete interference)

Insomnia = difficulty sleeping or falling asleep; patient reported 24-hour Insomnia was measured on 11-point NRS, (0 = no insomnia, 10 = worst possible insomnia)

Q.I.D. = four times a day

T.I.D. = three times daily

PGIC = Patient Global Impression of Change; 24-hour PGIC was measured on a seven-point bipolar (Likert) scale (1 = very much worse; 2 = much worse; 3 = minimally worse; 4 = no change; 5 = minimally improved; 6 = much improved; and 7 = very much improved)

Example 13: Naltrexone/Acetaminophen Open-Label Study for the Acute Treatment of Migraine (with Evaluation of Coexisting Emotional Pain)

Sixteen unique patients were enrolled in an open phase pilot study for the acute treatment of migraine attacks, insomnia, and emotional pain. Of the sixteen patients, eleven were evaluated for one migraine attack, one for two attacks, two for four attacks, one for six attacks, and one for fourteen attacks. A total of forty-one [N=42] treatments were evaluated. Patients received a single dose of one of the following treatment options:
 naltrexone/acetaminophen 1.5 mg/325 mg (N=1),
 naltrexone/acetaminophen 2.25 mg/325 mg (N=21),
 naltrexone/acetaminophen 3.25 mg/325 mg (N=3),
 naltrexone/acetaminophen 5 mg/325 mg (N=1)
 naltrexone 1.5 mg (N=3)
 naltrexone 2.25 mg (N=9),
 naltrexone 3.25 mg (N=3), or
 naltrexone 5 mg (N=1).

The majority of the patients remained in the clinic for observation for 2 hours after dosing. They completed headache diary assessments immediately before and after dosing at time points: 7, 15, and 30 minutes; and 1, 1.5, 2, 3, 6, 12, 24, and 48 hours. Headache pain was assessed on a 4-point scale (0=none; 1=mild; 2=moderate; 3=severe). The assessment of photophobia, phonophobia, nausea, and neck/shoulder pain was assessed as present or absent. The assessment of emotional pain was recorded on a 4-point scale (0=none, 1=mild, 2=moderate, 3=severe). The assessment of difficulty sleeping or falling asleep (insomnia) was assessed on a 4-point scale (0=none, 1=mild, 2=moderate, 3=severe) at baseline, for the night before treatment and for the following nights at 24, and 48 hours. Patients recorded side effects severity at each time point. Patients recorded the time of the first rescue medication dose and all additional headache medications used within 48 hours. Patients were required to stay awake to record their assessments in the first 2 hours, sleeping was permitted thereafter. While asleep, assessments were completed according to patients' best estimation. For data analysis, it was assumed that a migraine attack is a unique patient. Patients were asked to specify (yes or no answer) to whether they experienced emotional pain symptoms such as: hurt feelings, sadness, fear, or anger. Patients who replied positively to having emotional pain were asked to specify the cause into one of the following options: relationship, work/school, money/debt, health, or loss/grief.

Baseline Time Point Data

Baseline data were evaluated for balance between the groups. At baseline, there appeared to be a balance for headache pain-relief, headache pain-free, photophobia-free, phonophobia-free, nausea-free, and neck/shoulder pain-free. At baseline, naltrexone/acetaminophen 2.25 mg/325 mg (N=21) vs. naltrexone 2.25 mg (N=9) for insomnia-free and emotional pain-free was 24% and 48% vs. 44% and 67%, which represents baseline imbalance.

TABLE 10

| | naltrexone/acetaminophen doses and naltrexone doses at baseline (time-0) | | | | | | | | |
|---|---|---|---|---|---|---|---|---|---|
| 0' | NTX/APAP 1.5 mg/325 mg (N = 1) | NTX 1.5 mg (N = 3) | NTX/APAP 2.25 mg/325 mg (N = 21) | NTX 2.25 mg (N = 9) | NTX/APAP 3.25 mg/325 mg (N = 3) | NTX 3.25 mg (N = 3) | NTX/APAP 5 mg/325 mg (N = 1) | NTX 5 mg (N = 1) | p-value |
| Headache pain-relief-n (%) | 0 | 0 | 0 | 0 | 0 | 0 | 0 | 0 | |
| Headache pain-free-n (%) | 0 | 0 | 0 | 0 | 0 | 0 | 0 | 0 | |
| Photophobia-free-n (%) | 0 | 0 | 1 (5) | 1 (11) | 0 | 0 | 0 | 0 | 0.5564 |
| Phonophobia-free-n (%) | 1 | 0 | 3 (14) | 2 (22) | 0 | 0 | 1 | 0 | 0.5939 |
| Nausea-free-n (%) | 1 | 2 (66) | 7 (33) | 3 (38) | 3 (100) | 0 | 1 | 0 | 0.7952 |
| Neck/shoulder pain-free-n (%) | 0 | 0 | 7 (33) | 2 (22) | 0 | 1 | 0 | 0 | 0.5525 |
| Most bothersome symptom free-n (%) | 0 | 0 | 0 | 0 | 0 | 0 | 0 | 0 | |
| Insomnia free | 1 | 2 (66) | 5 (24) | 4 (44) | 1 (33) | 1 | 0 | 0 | 0.2815 |
| Emotional pain-free-n (%) | 1 | 2 (66) | 10 (48) | 6 (67) | 2 (66) | 1 | 0 | 0 | 0.3470 |
| AEs present | 0 | 0 | 0 | 0 | 0 | 0 | 0 | 0 | |
| Additional meds present | 0 | 0 | 0 | 0 | 0 | 0 | 0 | 0 | |

Headache pain-relief: score ≤1;
Headache pain-free: score = 0.
*p-value for NTX/APAP 2.25 mg/325 mg vs. NTX 2.25 mg, p-values were not calculated in logistic regression.

TABLE 11

Combined NTX/APAP doses and combined NTX doses at baseline (time-0)

| 0' | NTX/APAP (N = 26) | All NTX (N = 16) | p-value |
|---|---|---|---|
| Headache pain-relief-n (%) | 0 | 0 | |
| Headache pain-five-n (%) | 0 | 0 | |
| Photophobia-free-n (%) | 0 | 1 (6) | |
| Phonophobia-free-n (%) | 1 (4) | 2 (12) | |
| Nausea-free-n (%) | 8 (32) | 8 (50) | 0.2549 |
| Neck/shoulder pain-free-n (%) | 8 (32) | 2 (12) | |
| Most bothersome symptom free-n (%) | 0 | 0 | |
| Insomnia-free | 6 (24) | 7 (48) | 0.1163 |
| Emotional pain-free | 12 (48) | 10 (63) | 0.3532 |
| AEs present | 0 | 0 | |
| Additional meds present | 0 | 0 | |

7-Minute Time Point Data

At 7-minute time point has data for 25 migraine attacks (the rest of the time points have data on 42 migraine attacks), as data collection for this time point began while the study was in progress. At 7-minutes, Naltrexone/acetaminophen 2.25 mg/325 mg (N=15) vs. Naltrexone 2.25 mg (N=3) for headache pain-free and for most bothersome symptom-free was 27% and 27% vs. 0% and 0%. The 7-minutes data suggest earlier onset of action of the combination product vs. its component naltrexone.

TABLE 12 naltrexone/acetaminophen doses and naltrexone doses at 7 minutes

| 7' | NTX/APAP 1.5 mg/325 mg (N = 1) | NTX 1.5 mg (N = 0) | NTX/APAP 2.25 mg/325 mg (N = 15) | NTX 2.25 mg (N = 3) | NTX/APAP 3.25 mg/325 mg (N = 3) | NTX 3.25 mg (N = 2) | NTX/APAP 5 mg/325 mg (N = 1) | NTX 5 mg (N = 1) |
|---|---|---|---|---|---|---|---|---|
| Headache pain-relief-n (%) | 0 | n/a | 4 (27) | 0 (0) | 0 | 0 | 1 | 0 |
| Headache pain-free-n (%) | 0 | n/a | 0 (0) | 0 (0) | 0 | 0 | 0 | 0 |
| Photophobia-free-n (%) | 0 | n/a | 4 (27) | 0 (0) | 1 | 1 | 0 | 0 |
| Phonophobia-free-n (%) | 1 | n/a | 7 (47) | 2 (67) | 1 | 0 | 1 | 0 |
| Nausea-free-n (%) | 1 | n/a | 9 (60) | 0 (0) | 1 | 2 | 1 | 0 |
| Neck/shoulder pain-free-n (%) | 0 | n/a | 11 (73) | 2 (67) | 1 | 0 | 1 | 0 |
| Most bothersome symptom free-n (%) | 0 | n/a | 4 (27) | 0 (0) | 1 | 0 | 0 | 0 |
| Emotional pain-free-n (%) | 1 | n/a | 7 (47) | 1 (33) | 1 | 1 | 0 | 0 |
| Additional meds taken | 0 | n/a | 0 | 0 (0) | 0 | 0 | 0 | 0 |
| AEs present | 0 | n/a | 1 (7) | 0 (0) | 0 | 0 | 0 | 1 |

Headache pain-relief: score ≤1.

Headache pain-free: score = 0.

Collection of 7-minute time point began while the study was in progress, 25 of the 42 migraine attacks have data at this time point.

TABLE 13

Combined NTX/acetaminophen doses and combined NTX doses at 7 minutes

| 7' | All NTX/APAP (N = 20) | All NTX (N = 6) |
|---|---|---|
| Headache pain-relief-n (%) | 5 (25) | 0 (0) |
| Headache pain-free-n (%) | 0 (0) | 0 (0) |
| Photophobia-free-n (%) | 5 (26) | 1 (16) |
| Phonophobia-free-n (%) | 9 (47) | 2 (33) |
| Nausea-free-n (%) | 11 (58) | 2 (33) |
| Neck/shoulder pain-free-n (%) | 13 (68) | 2 (33) |
| Most bothersome symptom free-n (%) | 5 (26) | 0 (0) |
| Emotional pain-free-n (%) | 5 (36) | 2 (33) |
| Additional meds taken | 0 (0) | 0 (0) |
| AEs present | 1 (5) | 1 (16) |

Headache pain-relief: score ≤ 1;
Headache pain-free: score = 0.
Collection of 7-minute time point began while the study was in progress, 25 of the 42 migraine attacks have data at this time point.

15-Minute Time Point Data

At 15-minutes, naltrexone/acetaminophen 2.25 mg/325 mg (N=21) vs. naltrexone 2.25 mg (N=9) for headache pain-relief, headache pain-free, and most bothersome symptom-free was 76%, 29%, and 71% vs. 44%, 0%, and 11%. At 15-minutes, the combination product vs. its component, naltrexone shows superiority for headache pain-relief, headache pain-free and for most bothersome symptom-free.

TABLE 14 naltrexone/acetaminophen doses and naltrexone doses at 15 minutes

| 15' | NTX/APAP 1.5 mg/325 mg (N = 1) | NTX 1.5 mg (N = 3) | NTX/APAP 2.25 mg/325 mg (N = 21) | NTX 2.25 mg (N = 9) | NTX/APAP 3.25 mg/325 mg (N = 3) | NTX 3.25 mg (N = 3) | NTX/APAP 5 mg/325 mg (N = 1) | NTX 5 mg (N = 1) |
|---|---|---|---|---|---|---|---|---|
| Headache pain-relief-n (%) | 1 | 1 | 16 (76) | 4 (44) | 2 | 2 | 1 (100) | 0 |
| Headache pain-free-n (%) | 0 | 0 | 6 (29) | 0 (0) | 0 | 0 | 0 | 0 |
| Photophobia-free-n (%) | 0 | 0 | 13 (62) | 3 (33) | 1 | 1 | 1 (100) | 0 |
| Phonophobia-free-n (%) | 1 | 0 | 16 (76) | 4 (44) | 2 | 0 | 1 (100) | 0 |
| Nausea-free-n (%) | 1 | 2 | 18 (86) | 3 (33) | 2 | 3 | 1 (100) | 0 |
| Neck/shoulder pain-free-n (%) | 0 | 1 | 16 (76) | 4 (44) | 2 | 0 | 0 | 0 |
| Most bothersome symptom free-n (%) | 0 | 0 | 15 (71) | 1 (11) | 2 | 0 | 0 | 0 |
| Emotional pain-free-n (%) | 1 | 2 | 14 (66) | 7 (77) | 2 | 2 | 0 | 0 |
| Additional meds taken | 0 | 0 | 0 (0) | 0 (0) | 0 | 0 | 0 | 1 |
| AEs present | 0 | 0 | 3 (14) | 1 (11) | 0 | 0 | 0 | 0 |

Headache pain-relief: score ≤1; Headache pain-free: score = 0

TABLE 15

Combined naltrexone/APAP doses and combined naltrexone doses at 15 minutes

| 15' | Combined NTX/APAP (N = 26) | Combined NTX (N = 16) |
|---|---|---|
| Headache pain-relief-n (%) | 15 (70) | 7 (44) |
| Headache pain-free-n (%) | 3 (15) | 0 (0) |
| Photophobia-free-n (%) | 10 (50) | 4 (25) |
| Phonophobia-free-n (%) | 15 (70) | 4 (25) |
| Nausea-free-n (%) | 18 (85) | 8 (50) |
| Neck/shoulder pain-free-n (%) | 14 (70) | 5 (31) |
| Most bothersome symptom free-n (%) | 13 (65) | 1 (6) |
| Emotional pain-free-n (%) | 13 (65) | 11 (69) |
| Additional meds taken | 0 (0) | 0 (0) |
| AEs present | 3 (15) | 2 (13) |

Headache pain-relief: score ≤ 1;
Headache pain-free: score = 0

30-Minute Time Point Data

At 30-minutes, naltrexone/acetaminophen 2.25 mg/325 mg (N=21) vs. naltrexone 2.25 mg (N=9) for headache pain-relief, headache pain-free, and most bothersome symptom-free, was 90%, 76%, and 90% vs. 78%, 22% and 67%. At 30-minutes, naltrexone/acetaminophen 2.25 mg/325 mg (N=21) vs. naltrexone/acetaminophen 3.25 mg/325 mg (N=3) for headache pain-relief, headache pain-free and most bothersome symptom-free was 90%, 76%, and 90% vs. 66%, 66%, and 66%. At 30-minutes for naltrexone 1.5 mg (N=3), naltrexone 2.25 mg (N=3) and naltrexone 3.25 mg (N=3) for headache pain-free was 0%, 22%, and 0% respectively. At 30 minutes, the combination is superior to naltrexone 2.25 mg for headache pain-free (76% vs. 22%), while the two dosages of the combination appear equal.

TABLE 16 naltrexone/APAP doses and naltrexone doses at 30 minutes

| 30' | NTX/APAP 1.5 mg/325 mg (N = 1) | NTX 1.5 mg (N = 3) | NTX/APAP 2.25 mg/325 mg (N = 21) | NTX 2.25 mg (N = 9) | NTX/APAP 3.25 mg/325 mg (N = 3) | NTX 3.25 mg (N = 3) | NTX/APAP 5 mg/325 mg (N = 1) | NTX 5 mg (N = 1) | p-value* |
|---|---|---|---|---|---|---|---|---|---|
| Headache pain-relief-n (%) | 1 (100) | 2 (66) | 19 (90) | 7 (78) | 2 (66) | 2 (66) | 1 (100) | 0 (0) | 0.3876 |
| Headache pain-free-n (%) | 1 (100) | 0 (0) | 16 (76) | 2 (22) | 2 (66) | 0 (0) | 1 (100) | 0 (0) | 0.0066 |
| Photophobia-free-n (%) | 1 (100) | 0 (0) | 19 (90) | 5 (56) | 2 (66) | 1 (33) | 1 (100) | 1 (100) | 0.0366 |
| Phonophobia-free-n (%) | 1 (100) | 0 (0) | 16 (100) | 7 (78) | 2 (66) | 0 (0) | 1 (100) | 1 (100) | 0.0288 |
| Nausea-free-n (%) | 1 (100) | 2 (66) | 20 (95) | 8 (88) | 2 (66) | 2 (66) | 1 (100) | 0 (0) | 0.5012 |
| Neck/shoulder pain-free-n (%) | 1 (100) | 1 (33) | 20 (95) | 6 (67) | 2 (66) | 0 (0) | 1 (100) | 1 (100) | 0.0425 |
| Most bothersome symptom free-n (%) | 0 (0) | 0 (0) | 19 (90) | 6 (67) | 2 (66) | 0 (0) | 1 (100) | 0 (0) | 0.1299 |
| Emotional pain-free-n (%) | 1 (100) | 2 (66) | 16 (76) | 8 (89) | 2 (66) | 2 (66) | 1 (100) | 1 (100) | 0.4234 |
| Additional meds taken | 0 (0) | 0 (0) | 0 (0) | 0 | 0 (0) | 0 (0) | 0 | 0 (0) | |
| AEs present | 0 (0) | 0 (0) | 2 (10) | 1 (11) | 0 (0) | 2 (66) | 0 | 1 (100) | 0.9353 |

*p-value for NTX/APAP 2.25 mg/325 mg vs. NTX 2.25 mg, p-values were not calculated in logistic regression.

TABLE 17

Combined naltrexone/APAP doses and combined naltrexone doses at 30 minutes

| 30' | All NTX/APAP (N = 26) | All NTX (N = 16) | p-value |
|---|---|---|---|
| Headache pain-relief-n (%) | 23 (88) | 10 (63) | 0.0616 |
| Headache pain-free-n (%) | 20 (77) | 2 (13) | 0.0001 |
| Photophobia-free-n (%) | 23 (88) | 7 (48) | 0.0058 |
| Phonophobia-free-n (%) | 25 (96) | 8 (50) | 0.0006 |
| Nausea-free-n (%) | 24 (92) | 12 (75) | 0.1378 |
| Neck/shoulder pain-free-n (%) | 24 (92) | 8 (50) | 0.0025 |
| Most bothersome symptom-free-n (%) | 23 (88) | 6 (38) | 0.0009 |
| Emotional pain-free-n (%) | 20 (77) | 13 (87) | 0.3936 |
| Additional meds taken | 0 (0) | 0 (0) | |
| AEs present | 2 (8) | 4 (25) | 0.1378 |

Headache pain-relief: score ≤ 1.
Headache pain-free: score = 0.
*p-value were not calculated in logistic regression.

1-Hour Time Point Data

At 1-hour, naltrexone/acetaminophen 2.25 mg/325 mg (N=21) vs. naltrexone 2.25 mg (N=9) for headache pain-relief, headache pain-free, and most bothersome symptom-free, was 95%, 86%, and 95% vs. 88%, 44% and 77%. At 1-hour, naltrexone/acetaminophen 2.25 mg/325 mg (N=21) vs. naltrexone/acetaminophen 3.25 mg/325 mg (N=3) for headache pain-free and most bothersome symptom-free it was 86% and 95% vs. 66% vs. 77%. At 1-hour headache pain-free for naltrexone 1.5 mg (N=3), naltrexone 2.25 mg (N=3) and naltrexone 3.25 mg (N=3) was 33%, 44%, and 100% respectively. At 1-hour, the naltrexone/acetaminophen 2.25 mg/325 mg is superior (two-fold) to naltrexone 2.25 mg for headache pain-free (86% vs. 44%), while the two dosages of the combination appear equal.

TABLE 18 naltrexone/acetaminophen doses and naltrexone doses at 1 hour

| 1 h | NTX/APAP 1.5 mg/325 mg (N = 1) | NTX 1.5 mg (N = 3) | NTX/APAP 2.25 mg/325 mg (N = 21) | NTX 2.25 mg (N = 9) | NTX/APAP 3.25 mg/325 mg (N = 3) | NTX 3.25 mg (N = 3) | NTX/APAP 5 mg/325 mg (N = 1) | NTX 5 mg (N = 1) | p-value |
|---|---|---|---|---|---|---|---|---|---|
| Headache pain-relief-n (%) | 1 (100) | 2 (66) | 20 (95) | 8 (88) | 3 (100) | 3 (100) | 1 (100) | 1 | |
| Headache pain-free-n (%) | 1 (100) | 1 (33) | 18 (86) | 4 (44) | 2 (66) | 3 (100) | 1 (100) | 0 | 0.0190 |

TABLE 18-continued naltrexone/acetaminophen doses and naltrexone doses at 1 hour

| 1 h | NTX/APAP 1.5 mg/325 mg (N = 1) | NTX 1.5 mg (N = 3) | NTX/APAP 2.25 mg/325 mg (N = 21) | NTX 2.25 mg (N = 9) | NTX/APAP 3.25 mg/325 mg (N = 3) | NTX 3.25 mg (N = 3) | NTX/APAP 5 mg/325 mg (N = 1) | NTX 5 mg (N = 1) | p-value |
|---|---|---|---|---|---|---|---|---|---|
| Photophobia-free-n (%) | 1 (100) | 2 (66) | 20 (95) | 6 (66) | 3 (100) | 1 (33) | 1 (100) | 1 | |
| Phonophobia-free-n (%) | 1 (100) | 1 (33) | 21 (100) | 8 (88) | 3 (100) | 2 (66) | 1 (100) | 1 | |
| Nausea-free-n (%) | 1 (100) | 3 (100) | 21 (100) | 9 (100) | 3 (100) | 3 (100) | 1 (100) | 1 | |
| Neck/shoulder pain-free-n (%) | 1 (100) | 2 (66) | 21 (100) | 6 (66) | 3 (100) | 3 (100) | 1 (100) | 1 | |
| Most bothersome symptom free-n (%) | 1 (100) | 1 (33) | 20 (95) | 7 (77) | 3 (100) | 2 (66) | 1 (100) | 1 | |
| Emotional pain-free-n (%) | 1 (100) | 2 (66) | 17 (81) | 9 (100) | 2 (66) | 2 (66) | 1 (100) | 1 | |
| Additional meds taken | 0 | 0 | 0 | 0 (0) | 0 | 0 | 0 | 0 | |
| AEs present | 0 | 0 | 1 (5) | 1 (11) | 0 | 1 | 0 | 1 | |

Headache pain-relief: score ≤1; Headache pain-free: score = 0.
*p-value for NTX/APAP 2.25 mg/325 mg vs. NTX 2.25 mg, p-values were not calculated in logistic regression.

TABLE 19

Combined naltrexone/APAP doses and combined naltrexone doses at 1 hour

| 1 h | NTX/APAP (N = 26) | NTX (N = 16) | p-value |
|---|---|---|---|
| Headache pain-relief-n (%) | 25 (96) | 13 (81) | |
| Headache pain-free-n(%) | 22 (84) | 8 (50) | 0.0211 |
| Photophobia-free-n (%) | 25 (96) | 10 (63) | |
| Phonophobia-free-n (%) | 26 (100) | 12 (75) | |
| Nausea-free-n (%) | 26 (100) | 12 (75) | |
| Neck/shoulder pain-free-n (%) | 26 (100) | 12 (75) | |
| Most bothersome symptom free-n (%) | 25 (96) | 11 (69) | |
| Emotional pain-free-n (%) | 21 (80) | 14 (88) | |
| Additional meds taken | 0 | 0 | |
| AEs present | 1 (4) | 3 (19) | |

Headache pain-relief: score ≤ 1;
Headache pain-free: score = 0.
*p-value were not calculated in logistic regression.

90-Minute Time Point Data

At 90-minutes, naltrexone/acetaminophen 2.25 mg/325 mg (N=21) vs. naltrexone 2.25 mg (N=9) for headache pain-relief, headache pain-free, and most bothersome symptom-free was 94%, 86% and 90% vs. 100%, 77%, and 100%. At 90-minutes, naltrexone/acetaminophen 2.25 mg/325 mg (N=21) vs. naltrexone/acetaminophen 3.25 mg/325 mg (N=3) for headache pain-free, and most bothersome symptom-free was 86% and 90% vs. 77% and 100%. At 90-minutes, headache pain-free for naltrexone 1.5 mg (N=3), naltrexone 2.25 mg (N=3) and naltrexone 3.25 mg (N=3) was 100%, 100%, and 100% respectively. At 90-minutes, the combination vs. naltrexone alone (all dosages) appear equal in all assessments. Additionally, the two dosages of the combination appear equal.

TABLE 20 naltrexone/acetaminophen doses and naltrexone doses at 90 minutes

| 90' | NTX/APAP 1.5 mg/325 mg (N = 1) | NTX 1.5 mg (N = 3) | NTX/APAP 2.25 mg/325 mg (N = 21) | NTX 2.25 mg (N = 9) | NTX/APAP 3.25 mg/325 mg (N = 3) | NTX 3.25 mg (N = 3) | NTX/APAP 5 mg/325 mg (N = 1) | NTX 5 mg (N = 1) |
|---|---|---|---|---|---|---|---|---|
| Headache pain-relief-n (%) | 1 (100) | 3 (100) | 20 (94) | 9 (100) | 3 (100) | 3 (100) | 1 (100) | 1 (100) |
| Headache pain-free-n (%) | 1 (100) | 1 (33) | 18 (86) | 7 (77) | 3 (100) | 3 (100) | 1 (100) | 1 (100) |
| Photophobia-free-n (%) | 1 (100) | 1 (100) | 19 (90) | 8 (88) | 3 (100) | 2 (66) | 1 (100) | 1 (100) |
| Phonophobia-free-n (%) | 1 (100) | 1 (100) | 21 (100) | 9 (100) | 3 (100) | 2 (66) | 1 (100) | 1 (100) |
| Nausea-free-n (%) | 1 (100) | 3 (100) | 21 (100) | 9 (100) | 3 (100) | 2 (66) | 1 (100) | 1 (100) |
| Neck/shoulder pain-free-n (%) | 1 (100) | 1 (33) | 21 (100) | 9 (100) | 3 (100) | 3 (100) | 1 (100) | 1 (100) |
| Most bothersome symptom free-n (%) | 1 (100) | 2 (66) | 19 (90) | 9 (100) | 3 (100) | 2 (66) | 1 (100) | 1 (100) |
| Emotional pain-free-n (%) | 1 (100) | 3 (100) | 18 (86) | 9 (100) | 3 (100) | 3 (100) | 1 (100) | 1 (100) |
| Additional meds taken | 0 (0) | 0 (0) | 0 (0) | 0 (0) | 0 (0) | 0 (0) | 0 | 0 (0) |
| AEs present | 0 (0) | 0 (0) | 1 (5) | 0 (0) | 0 (0) | 1 (33) | 0 | 1 (100) |

TABLE 21

Combined NTX/acetaminophen doses and combined NTX doses at 90 minutes

| 90' | NTX/APAP (N = 26) | NTX (N = 16) |
|---|---|---|
| Headache pain-relief-n (%) | 25 (96) | 16 (100) |
| Headache pain-free-n (%) | 23 (88) | 13 (81) |
| Photophobia-free-n (%) | 24 (92) | 12 (75) |
| Phonophobia-free-n (%) | 26 (100) | 13 (81) |
| Nausea-free-n (%) | 26 (100) | 16 (100) |
| Neck/shoulder pain-free-n (%) | 26 (100) | 14 (88) |
| Most bothersome symptom free-n (%) | 24 (92) | 14 (88) |
| Emotional pain-free-n (%) | 23 (88) | 16 (100) |
| Additional meds taken | 0 (0) | 0 |
| LAEs present | 1 (5) | 2 (13) |

2-Hour Time Point Data

At 2-hours, naltrexone/acetaminophen 2.25 mg/325 mg (N=21) vs. naltrexone 2.25 mg (N=9) for headache pain-relief, headache pain-free, and most bothersome symptom-free, was 100%, 90%, and 95% vs. 100%, 77% and 100%. At 2-hours, naltrexone/acetaminophen 2.25 mg/325 mg (N=21) vs. naltrexone/acetaminophen 3.25 mg/325 mg (N=3) for headache pain-free, and for most bothersome symptom-free, was 90% and 95% vs. 77% and 100%. At 2-hours, headache pain-free for naltrexone 1.5 mg (N=3), naltrexone 2.25 mg (N=3) and naltrexone 3.25 mg (N=3) was 100%, 100%, and 100% respectively. At 2-hours, there appear to be approximately 100% headache pain-free and associated symptoms for the combinations and for naltrexone alone. The two dosages of the combination appear equal in efficacy but the higher dose has AEs 33% vs. 10%.

TABLE 22 naltrexone/APAP doses and naltrexone doses at 2 hour

| 2 h | NTX/APAP 1.5 mg/325 mg (N = 1) | NTX 1.5 mg (N = 3) | NTX/APAP 2.25 mg/325 mg (N = 21) | NTX 2.25 mg (N = 9) | NTX/APAP 3.25 mg/325 mg (N = 3) | NTX 3.25 mg (N = 3) | NTX/APAP 5 mg/325 mg (N = 1) | NTX 5 mg (N = 1) |
|---|---|---|---|---|---|---|---|---|
| Headache pain-relief-n (%) | 1 (100) | 3 (100) | 21 (100) | 9 (100) | 3 (100) | 3 (100) | 1 (100) | 1 |
| Headache pain-free-n (%) | 1 (100) | 3 (100) | 19 (90) | 7 (77) | 3 (100) | 3 (100) | 1 (100) | 1 |
| Photophobia-free-n (%) | 1 (100) | 3 (100) | 20 (95) | 8 (88) | 3 (100) | 3 (100) | 1 (100) | 1 |
| Phonophobia-free-n (%) | 1 (100) | 3 (100) | 21 (100) | 9 (100) | 3 (100) | 3 (100) | 1 (100) | 1 |
| Nausea-free-n (%) | 1 (100) | 3 (100) | 21 (100) | 9 (100) | 3 (100) | 3 (100) | 1 (100) | 1 |
| Neck/shoulder pain-free-n (%) | 1 (100) | 3 (100) | 21 (100) | 9 (100) | 3 (100) | 3 (100) | 1 (100) | 1 |
| Most bothersome symptom free-n (%) | 1 (100) | 3 (100) | 20 (95) | 9 (100) | 3 (100) | 3 (100) | 1 (100) | 1 |
| Emotional pain-free-n (%) | 1 (100) | 3 (100) | 18 (86) | 9 (100) | 3 (100) | 3 (100) | 1 (100) | 1 |
| Additional meds taken | 0 | 0 | 0 | 0 | 0 | 0 | 0 | 0 |
| AEs present | 0 | 0 (0) | 2 (10) | 0 (0) | 0 | 1 (33) | 0 | 1 |

Headache pain-relief: score ≤1; Headache pain-free: score = 0

TABLE 23

Combined naltrexone/APAP doses and combined naltrexone doses at 2 hours

| 2 h | NTX/APAP (N = 26) | NTX (N = 16) |
|---|---|---|
| Headache pain-relief-n (%) | 26 (100) | 16 (100) |
| Headache pain-free-n (%) | 24 (92) | 14 (88) |
| Photophobia-free-n (%) | 25 (96) | 16 (100) |
| Phonophobia-free-n (%) | 26 (100) | 16 (100) |
| Nausea-free-n (%) | 26 (100) | 16 (100) |
| Neck/shoulder pain-free-n (%) | 26 (100) | 16 (100) |

TABLE 23-continued

Combined naltrexone/APAP doses and combined naltrexone doses at 2 hours

| 2 h | NTX/APAP (N = 26) | NTX (N = 16) |
|---|---|---|
| Most bothersome symptom free-n (%) | 25 (96) | 16 (100) |
| Emotional pain-free | 23 (88) | 16 (100) |
| Additional meds taken | 0 | 0 |
| AEs present | 2 (8) | 2 (13) |

3-Hour Time Point Data

At 3-hours, naltrexone/acetaminophen 2.25 mg/325 mg (N=21) vs. naltrexone 2.25 mg (N=9) for headache pain-relief, headache pain-free, and most bothersome symptom-free was 100%, 95%, and 95% vs. 100%, 77% vs. 100%. At 3-hours, naltrexone/acetaminophen 2.25 mg/325 mg (N=21) vs. naltrexone/acetaminophen 3.25 mg/325 mg (N=3) for headache pain-free and for most bothersome symptom-free was 95% and 95% vs. 100% and 100%. At 3-hours, headache pain-free for naltrexone 1.5 mg (N=3), naltrexone 2.25 mg (N=3) and naltrexone 3.25 mg (N=3) was 100%, 100%, and 100% respectively. At 3-hours, there appear to be approximately 100% headache pain-free and associated symptoms for the combinations and for naltrexone alone. The two dosages of the combination appear equal in efficacy but the higher dose has AEs 33% vs. 0%.

TABLE 24 naltrexone/APAP doses and naltrexone doses at 3 hour

| 3 h | NTX/APAP 1.5 mg/325 mg (N = 1) | NTX 1.5 mg (N = 3) | NTX/APAP 2.25 mg/325 mg (N = 21) | NTX 2.25 mg (N = 9) | NTX/APAP 3.25 mg/325 mg (N = 3) | NTX 3.25 mg (N = 3) | NTX/APAP 5 mg/325 mg (N = 1) | NTX 5 mg (N = 1) |
|---|---|---|---|---|---|---|---|---|
| Headache pain-relief-n (%) | 1 | 3 (100) | 21 (100) | 9 (100) | 3 (100) | 3 (100) | 1 (100) | 1 (100) |
| Headache pain-free-n (%) | 1 | 3 (100) | 20 (95) | 7 (77) | 3 (100) | 3 (100) | 1 (100) | 1 (100) |
| Photophobia-free-n (%) | 1 | 3 (100) | 20 (95) | 8 (88) | 3 (100) | 3 (100) | 1 (100) | 1 (100) |
| Phonophobia-free-n (%) | 1 | 3 (100) | 20 (95) | 9 (100) | 3 (100) | 3 (100) | 1 (100) | 1 (100) |
| Nausea-free-n (%) | 1 | 3 (100) | 21 (100) | 9 (100) | 3 (100) | 3 (100) | 1 (100) | 1 (100) |
| Neck/shoulder pain-free-n (%) | 1 | 3 (100) | 21 (100) | 9 (100) | 3 (100) | 3 (100) | 1 (100) | 1 (100) |
| Most bothersome symptom free-n (%) | 1 | 3 (100) | 20 (95) | 9 (100) | 3 (100) | 3 (100) | 1 (100) | 1 (100) |
| Emotional pain-free-n (%) | | 3 (100) | 19 (90) | 9 (100) | 3 (100) | 3 (100) | 1 (100) | 1 (100) |
| Additional meds taken | 0 | 0 | 0 (0) | 0 (0) | 0 | 0 | 0 | 0 |
| AEs present | 0 | 0 | 0 (0) | 0 (0) | 0 | 1 (33) | 0 | 1 |

Headache pain-relief: score ≤1; Headache pain-free: score = 0

TABLE 25

Combined naltrexone/APAP doses and combined naltrexone doses at 3 hours

| 3 h | NTX/APAP (N = 26) | NTX (N = 16) |
|---|---|---|
| Headache pain-relief-n (%) | 26 (100) | 16 (100) |
| Headache pain-free-n (%) | 25 (96) | 14 (88) |
| Photophobia-free-n (%) | 24 (96) | 15 (94) |
| Phonophobia-free-n (%) | 26 (100) | 16 (100) |
| Nausea-free-n (%) | 26 (100) | 16 (100) |
| Neck/shoulder pain-free-n (%) | 26 (100) | 16 (100) |
| Most bothersome symptom free-n (%) | 25 (96) | 16 (100) |
| Emotional pain-free-n (%) | 243 (92) | 16 (100) |
| Additional meds taken | 0 | 0 |
| AEs present | 0 | 2 (13) |

4-Hour Time Point Data

At 4-hours, naltrexone/acetaminophen 2.25 mg/325 mg (N=21) vs. naltrexone 2.25 mg (N=9) for headache pain-relief, headache pain-free, and most bothersome symptom-free was 100%, 95%, and 100% vs. 88%, 66% vs. 88%. At 4-hours, naltrexone/acetaminophen 2.25 mg/325 mg (N=21) vs. naltrexone/acetaminophen 3.25 mg/325 mg (N=3) for headache pain-free and for most bothersome symptom-free was 95% and 100% vs. 100% and 100%. At 4-hours, headache pain-free for naltrexone 1.5 mg (N=3), naltrexone 2.25 mg (N=3) and naltrexone 3.25 mg (N=3) was 100%, 100%, and 100% respectively. At 4-hours, there appear to be approximately 100% headache pain-free and associated symptoms for the combinations and for naltrexone alone. The two dosages of the combination appear equal in efficacy but the higher dose has AEs 33% vs. 0%.

TABLE 26 naltrexone/APAP doses and naltrexone doses at 4 hour

| 4 h | NTX/APAP 1.5 mg/325 mg (N = 1) | NTX 1.5 mg (N = 3) | NTX/APAP 2.25 mg/325 mg (N = 21) | NTX 2.25 mg (N = 9) | NTX/APAP 3.25 mg/325 mg (N = 3) | NTX 3.25 mg (N = 3) | NTX/APAP 5 mg/325 mg (N = 1) | NTX 5 mg (N = 1) |
|---|---|---|---|---|---|---|---|---|
| Headache pain-relief-n (%) | 1 | 3 (100) | 21 (100) | 8 (88) | 3 (100) | 3 (100) | 1 (100) | 1 (100) |
| Headache pain-free-n (%) | 1 | 3 (100) | 20 (95) | 6 (66) | 3 (100) | 3 (100) | 1 (100) | 1 (100) |
| Photophobia-free-n (%) | 1 | 3 (100) | 21 (100) | 7 (77) | 3 (100) | 3 (100) | 1 (100) | 1 (100) |
| Phonophobia-free-n (%) | 1 | 3 (100) | 21 (100) | 8 (88) | 3 (100) | 3 (100) | 1 (100) | 1 (100) |
| Nausea-free-n (%) | 1 | 3 (100) | 21 (100) | 8 (88) | 3 (100) | 3 (100) | 1 (100) | 1 (100) |
| Neck/shoulder pain-free-n (%) | 1 | 3 (100) | 21 (100) | 9 (100) | 3 (100) | 3 (100) | 1 (100) | 1 (100) |
| Most bothersome symptom-free-n (%) | 1 | 3 (100) | 21 (100) | 8 (88) | 3 (100) | 3 (100) | 1 (100) | 1 (100) |
| Emotional pain-free-n (%) | 1 | 3 (100) | 19 (90) | 9 (100) | 3 (100) | 3 (100) | 1 (100) | 1 (100) |
| Additional meds taken | 0 | 0 | 0 (0) | 0 (0) | 0 | 0 | 0 | 0 |
| AEs present | 0 | 0 | 0 (0) | 0 (0) | 1 (33) | 1 (33) | 0 | 1 |

Headache pain-relief: score ≤1; Headache pain-free: score = 0

TABLE 27

Combined naltrexone/APAP doses and combined naltrexone doses at 4 hours

| 4 h | NTX/APAP (N = 26) | NTX (N = 16) |
|---|---|---|
| Headache pain-relief-n (%) | 26 (100) | 15 (94) |
| Headache pain-free-n (%) | 25 (96) | 13 (81) |
| Photophobia-free-n (%) | 26 (100) | 14 (88) |
| Phonophobia-free-n (%) | 26 (100) | 15 (94) |
| Nausea-free-n (%) | 26 (100) | 15 (94) |
| Neck/shoulder pain-free-n (%) | 26 (100) | 16 (100) |
| Most bothersome symptom-free-n (%) | 26 (100) | 15 (94) |
| Emotional pain-free-n (%) | 24 (92) | 15 (94) |
| Additional meds taken | 0 | 0 |
| AEs present | 1 (4) | 2 (13) |

6-Hour Time Point Data

At 6-hours, naltrexone/acetaminophen 2.25 mg/325 mg (N=21) vs. naltrexone 2.25 mg (N=9) for headache pain-relief, headache pain-free, and most bothersome symptom-free was 100%, 95%, and 100% vs. 100%, 77% vs. 100%. At 6-hours, naltrexone/acetaminophen 2.25 mg/325 mg (N=21) vs. naltrexone/acetaminophen 3.25 mg/325 mg (N=3) for headache pain-free and for most bothersome symptom-free was 95% and 100% vs. 100% and 100%. At 6-hours, headache pain-free for naltrexone 1.5 mg (N=3), naltrexone 2.25 mg (N=3) and naltrexone 3.25 mg (N=3) was 100%, 100%, and 100% respectively. At 6-hours, there appear to be approximately 100% headache pain-free and associated symptoms for the combinations and for naltrexone alone. The two dosages of the combination appear equal in efficacy but the higher dose has AEs 33% vs. 0%.

TABLE 28 naltrexone/APAP doses and naltrexone doses at 6 hour

| 6 h | NTX/APAP 1.5 mg/325 mg (N = 1) | NTX 1.5 mg (N = 3) | NTX/APAP 2.25 mg/325 mg (N = 21) | NTX 2.25 mg (N = 9) | NTX/APAP 3.25 mg/325 mg (N = 3) | NTX 3.25 mg (N = 3) | NTX/APAP 5 mg/325 mg (N = 1) | NTX 5 mg (N = 1) |
|---|---|---|---|---|---|---|---|---|
| Headache pain-relief-n (%) | 1 | 3 (100) | 21 (100) | 9 (100) | 3 (100) | 3 (100) | 1 (100) | 1 (100) |
| Headache pain-free-n (%) | 1 | 3 (100) | 20 (95) | 7 (77) | 3 (100) | 3 (100) | 1 (100) | 1 (100) |
| Photophobia-free-n (%) | 1 | 3 (100) | 21 (100) | 8 (88) | 3 (100) | 3 (100) | 1 (100) | 1 (100) |
| Phonophobia-free-n (%) | 1 | 3 (100) | 21 (100) | 9 (100) | 3 (100) | 3 (100) | 1 (100) | 1 (100) |
| Nausea-free-n (%) | 1 | 3 (100) | 21 (100) | 9 (100) | 3 (100) | 3 (100) | 1 (100) | 1 (100) |
| Neck/shoulder pain-free-n (%) | 1 | 3 (100) | 21 (100) | 9 (100) | 3 (100) | 3 (100) | 1 (100) | 1 (100) |
| Most bothersome symptom-free-n (%) | 1 | 3 (100) | 21 (100) | 9 (100) | 3 (100) | 3 (100) | 1 (100) | 1 (100) |
| Emotional pain-free-n (%) | 1 | 3 (100) | 19 (90) | 9 (100) | 3 (100) | 3 (100) | 1 (100) | 1 (100) |
| Additional meds taken | 0 | 0 | 0 (0) | 0 (0) | 0 | 0 | 0 | 0 |
| AEs present | 0 | 0 | 0 (0) | 0 (0) | 0 | 1 (33) | 0 | 1 |

Headache pain-relief: score ≤1; Headache pain-free: score = 0

TABLE 29

Combined naltrexone/APAP doses and combined naltrexone doses at 6 hours

| 6 h | NTX/APAP (N = 26) | NTX (N = 16) |
|---|---|---|
| Headache pain-relief-n (%) | 26 (100) | 16 (100) |
| Headache pain-free-n (%) | 25 (96) | 14 (88) |
| Photophobia-free-n (%) | 26 (100) | 15 (94) |
| Phonophobia-free-n (%) | 26 (100) | 16 (100) |
| Nausea-free-n (%) | 26 (100) | 16 (100) |
| Neck/shoulder pain-free-n (%) | 26 (100) | 16 (100) |
| Most bothersome symptom-free-n (%) | 26 (100) | 16 (100) |
| Emotional pain-free-n (%) | 24 (92) | 15 (94) |
| Additional meds taken | 0 | 0 |
| AEs present | 0 | 2 (13) |

12-Hour Time Point Data

At 12-hours, naltrexone/acetaminophen 2.25 mg/325 mg (N=21) vs. naltrexone 2.25 mg (N=9) for headache pain-relief, headache pain-free, and most bothersome symptom-free was 100%, 100%, and 100% vs. 100%, 77% vs. 100%. At 12-hours, naltrexone/acetaminophen 2.25 mg/325 mg (N=21) vs. naltrexone/acetaminophen 3.25 mg/325 mg (N=3) for headache pain-free and for most bothersome symptom-free was 100% and 100% vs. 100% and 100%. At 12-hours, headache pain-free for naltrexone 1.5 mg (N=3), naltrexone 2.25 mg (N=3) and naltrexone 3.25 mg (N=3) was 100%, 100%, and 100% respectively. At 12-hours, there appear to be approximately 100% headache pain-free and associated symptoms for the combinations and for naltrexone alone. The two dosages of the combination appear equal in efficacy but the higher dose has AEs 33% vs. 0%.

TABLE 30 naltrexone/APAP doses and naltrexone doses at 12 hour

| 12 h | NTX/APAP 1.5 mg/325 mg (N = 1) | NTX 1.5 mg (N = 3) | NTX/APAP 2.25 mg/325 mg (N = 21) | NTX 2.25 mg (N = 9) | NTX/APAP 3.25 mg/325 mg (N = 3) | NTX 3.25 mg (N = 3) | NTX/APAP 5 mg/325 mg (N = 1) | NTX 5 mg (N = 1) |
|---|---|---|---|---|---|---|---|---|
| Headache pain-relief-n (%) | 1 | 3 (100) | 16 (100) | 9 (100) | 3 (100) | 3 (100) | 1 (100) | 1 (100) |
| Headache pain-free-n (%) | 1 | 3 (100) | 16 (100) | 7 (77) | 3 (100) | 3 (100) | 1 (100) | 1 (100) |
| Photophobia-free-n (%) | 1 | 3 (100) | 16 (100) | 8 (88) | 3 (100) | 3 (100) | 1 (100) | 1 (100) |
| Phonophobia-free-n (%) | 1 | 3 (100) | 16 (100) | 9 (100) | 3 (100) | 3 (100) | 1 (100) | 1 (100) |
| Nausea-free-n (%) | 1 | 3 (100) | 16 (100) | 9 (100) | 3 (100) | 3 (100) | 1 (100) | 1 (100) |
| Neck/shoulder pain-free-n (%) | 1 | 3 (100) | 16 (100) | 9 (100) | 3 (100) | 3 (100) | 1 (100) | 1 (100) |
| Most bothersome symptom-free-n (%) | 1 | 3 (100) | 16 (100) | 9 (100) | 3 (100) | 3 (100) | 1 (100) | 1 (100) |
| Emotional pain-free-n (%) | 1 | 3 (100) | 19 (90) | 9 (100) | 3 (100) | 3 (100) | 1 (100) | 1 (100) |
| Additional meds taken | 0 | 0 | 0 (0) | 0 (0) | 0 | 0 | 0 | 0 |
| AEs present | 0 | 0 | 0 (0) | 0 (0) | 0 | 1 (33) | 0 | 1 |

Headache pain-relief: score ≤1; Headache pain-free: score = 0

TABLE 31

Combined naltrexone/APAP doses and combined naltrexone doses at 12 hours

| 12 h | NTX/APAP (N = 26) | NTX (N = 16) |
|---|---|---|
| Headache pain-relief-n (%) | 26 (100) | 16 (100) |
| Headache pain-free-n (%) | 26 (100) | 14 (88) |
| Photophobia-free-n (%) | 26 (100) | 15 (94) |
| Phonophobia-free-n (%) | 26 (100) | 16 (100) |
| Nausea-free-n (%) | 26 (100) | 16 (100) |
| Neck/shoulder pain-free-n (%) | 26 (100) | 16 (100) |
| Most bothersome symptom-free-n (%) | 26 (100) | 16 (100) |
| Emotional pain-free-n (%) | 24 (92) | 15 (94) |

TABLE 31-continued

Combined naltrexone/APAP doses and
combined naltrexone doses at 12 hours

| 12 h | NTX/APAP (N = 26) | NTX (N = 16) |
|---|---|---|
| Additional meds taken | 0 | 0 |
| AEs present | 0 | 2 (13) |

24-Hour Time Point Data

At 24-hours, naltrexone/acetaminophen 2.25 mg/325 mg (N=21) vs. naltrexone 2.25 mg (N=9) for headache pain-relief, headache pain-free, and most bothersome symptom-free was 100%, 100%, and 100% vs. 100%, 88% vs. 100%. At 24-hours, naltrexone/acetaminophen 2.25 mg/325 mg (N=21) vs. naltrexone/acetaminophen 3.25 mg/325 mg (N=3) for headache pain-free and for most bothersome symptom-free was 100% and 100% vs. 100% and 100%. At 24-hours, headache pain-free for naltrexone 1.5 mg (N=3), naltrexone 2.25 mg (N=3) and naltrexone 3.25 mg (N=3) was 100%, 100%, and 100% respectively. At 24-hours, there appear to be approximately 100% headache pain-free and associated symptoms for the combinations and for naltrexone alone. The two dosages of the combination appear equal in efficacy but the higher dose has AEs 33% vs. 0%.

TABLE 32 naltrexone/APAP doses and naltrexone doses at 24 hour

| 24 h | NTX/APAP 1.5 mg/325 mg (N = 1) | NTX 1.5 mg (N = 3) | NTX/APAP 2.25 mg/325 mg (N = 21) | NTX 2.25 mg (N = 9) | NTX/APAP 3.25 mg/325 mg (N = 3) | NTX 3.25 mg (N = 3) | NTX/APAP 5 mg/325 mg (N = 1) | NTX 5 mg (N = 1) |
|---|---|---|---|---|---|---|---|---|
| Headache pain-relief-n (%) | 1 | 3 (100) | 21 (100) | 9 (100) | 3 (100) | 3 (100) | 1 (100) | 1 (100) |
| Headache pain-free-n (%) | 1 | 3 (100) | 21 (100) | 8 (88) | 3 (100) | 3 (100) | 1 (100) | 1 (100) |
| Photophobia-free-n (%) | 1 | 3 (100) | 21 (100) | 9 (100) | 3 (100) | 3 (100) | 1 (100) | 1 (100) |
| Phonophobia-free-n (%) | 1 | 3 (100) | 21 (100) | 9 (100) | 3 (100) | 3 (100) | 1 (100) | 1 (100) |
| Nausea-free-n (%) | 1 | 3 (100) | 21 (100) | 9 (100) | 3 (100) | 3 (100) | 1 (100) | 1 (100) |
| Neck/shoulder pain-free-n (%) | 1 | 3 (100) | 21 (100) | 9 (100) | 3 (100) | 3 (100) | 1 (100) | 1 (100) |
| Most bothersome symptom-free-n (%) | 1 | 3 (100) | 21 (100) | 9 (100) | 3 (100) | 3 (100) | 1 (100) | 1 (100) |
| Insomnia-free-n (%) | 1 | 2 (66) | 3 (14) | 6 (66) | 3 (100) | 2 (66) | 1 (100) | 1 (100) |
| Emotional pain-free-n (%) | 1 | 3 (100) | 19 (90) | 9 (100) | 3 (100) | 3 (100) | 1 (100) | 1 (100) |
| Additional meds taken | 0 | 0 | 0 | 0 | 0 | 0 | 0 | 0 |
| AEs present | 0 | 0 | 0 | 0 | 0 | 1 (33) | 0 | 1 |

Headache pain-relief: score ≤1; Headache pain-free: score = 0.
For consistency of data, the insomnia score will be marked at the 24-time point for the night following the day of initial dosing.

TABLE 33

Combined naltrexone/APAP doses and
combined naltrexone doses at 24 hours

| 24 h | NTX/APAP (N = 26) | NTX (N = 16) |
|---|---|---|
| Headache pain-relief-n (%) | 26 (100) | 16 (100) |
| Headache pain-free-n (%) | 26 (100) | 15 (94) |
| Photophobia-free-n (%) | 26 (100) | 16 (100) |
| Phonophobia-free-n (%) | 26 (100) | 16 (100) |
| Nausea-free-n (%) | 26 (100) | 16 (100) |
| Neck/shoulder pain-free-n (%) | 26 (100) | 16 (100) |
| Most bothersome symptom-free-n (%) | 26 (100) | 16 (100) |
| Insomnia-free-n (%) | 22 (84) | 11 (69) |
| Emotional pain-free | 22 (92) | 15 (94) |
| Additional meds taken | 0 | 0 |
| AEs present | 0 | 2 (13) |

48-Hour Time Point Data

At 48-hours, naltrexone/acetaminophen 2.25 mg/325 mg (N=21) vs. naltrexone 2.25 mg (N=9) for headache pain-relief, headache pain-free, and most bothersome symptom-free was 95%, 95%, and 100% vs. 100%, 100% vs. 100%. At 48-hours, naltrexone/acetaminophen 2.25 mg/325 mg (N=21) vs. naltrexone/acetaminophen 3.25 mg/325 mg (N=3) for headache pain-free and for most bothersome symptom-free was 95% and 100% vs. 100% and 100%. At 48-hours, headache pain-free for naltrexone 1.5 mg (N=3), naltrexone 2.25 mg (N=3) and naltrexone 3.25 mg (N=3) was 100%, 100%, and 100% respectively. At 48-hours, there appear to be approximately 100% headache pain-free and associated symptoms for the combinations and for naltrexone alone. The two dosages of the combination appear equal in efficacy but the higher dose has AEs 33% vs. 0%.

TABLE 34 naltrexone/APAP doses and naltrexone doses at 48 hour

| 48 h | NTX/APAP 1.5 mg/325 mg (N = 1) | NTX 1.5 mg (N = 3) | NTX/APAP 2.25 mg/325 mg (N = 21) | NTX 2.25 mg (N = 9) | NTX/APAP 3.25 mg/325 mg (N = 3) | NTX 3.25 mg (N = 3) | NTX/APAP 5 mg/325 mg (N = 1) | NTX 5 mg (N = 1) |
|---|---|---|---|---|---|---|---|---|
| Headache pain-relief-n (%) | 1 | 2 (66) | 20 (95) | 9 (100) | 3 (100) | 3 (100) | 1 (100) | 1 (100) |
| Headache pain-free-n (%) | 1 | 2 (66) | 20 (95) | 9 (100) | 3 (100) | 3 (100) | 1 (100) | 1 (100) |
| Photophobia-free-n (%) | 1 | 2 (66) | 21 (100) | 9 (100) | 3 (100) | 3 (100) | 1 (100) | 1 (100) |
| Phonophobia-free-n (%) | 1 | 3 (100) | 21 (100) | 9 (100) | 3 (100) | 3 (100) | 1 (100) | 1 (100) |
| Nausea-free-n (%) | 1 | 2 (66) | 21 (100) | 9 (100) | 3 (100) | 3 (100) | 1 (100) | 1 (100) |
| Neck/shoulder pain-free-n (%) | 1 | 3 (100) | 21 (100) | 9 (100) | 3 (100) | 3 (100) | 1 (100) | 1 (100) |
| Most bothersome symptom-free-n (%) | 1 | 2 (66) | 21 (100) | 9 (100) | 3 (100) | 3 (100) | 1 (100) | 1 (100) |
| Insomnia-free-n (%) | | | 18 (86) | 8 (88) | | | 1 (100) | 1 (100) |
| Emotional pain-free | 1 | 3 (100) | 19 (90) | 9 (100) | 3 (100) | 3 (100) | 1 (100) | 1 (100) |
| Additional meds taken | 0 | 0 | 0 (0) | 0 (0) | 0 | 0 | 0 | 1 |
| AEs present | 0 | 0 | 0 (0) | 0 (0) | 0 | 1 (33) | 0 | 0 |

Headache pain-relief: score ≤1; Headache pain-free: score = 0

TABLE 35

Combined naltrexone/APAP doses and combined naltrexone doses at 48 hours

| 48 h | NTX/APAP (N = 26) | NTX (N = 16) |
|---|---|---|
| Headache pain-relief-n (%) | 25 (96) | 15 (94) |
| Headache pain-free-n (%) | 25 (96) | 15 (94) |
| Photophobia-free-n (%) | 26 (100) | 15 (94) |
| Phonophobia-free-n (%) | 26 (100) | 16 (100) |
| Nausea-free-n (%) | 26 (100) | 15 (94) |
| Neck/shoulder pain-free-n (%) | 26 (100) | 16 (100) |
| Most bothersome symptom-free-n (%) | 26 (100) | 15 (94) |
| Insomnia-free-n (%) | 23 (88) | 2 (13) |
| Emotional pain-free-n (%) | 24 (92) | 13 (100) |
| Additional meds taken | 0 | 1 |
| AEs present | 0 | 1 |

Insomnia Data

In the night after dosing, naltrexone/acetaminophen 2.25 mg/325 mg (N=21) vs. naltrexone 2.25 mg (N=9) for insomnia-free change from baseline was 57% vs. 22%, and for insomnia intensity, the change from baseline was (−142%) vs. (−111%). The data suggests beneficial effect of the combination and of naltrexone on insomnia with advantage for the combination.

TABLE 36 naltrexone/APAP doses and naltrexone doses for insomnia-free at baseline and night post-dosing

| Insomnia-free | NTX/APAP 1.5 mg/325 mg (N = 1) | NTX 1.5 mg (N = 3) | NTX/APAP 2.25 mg/325 mg (N = 21) | NTX 2.25 mg (N = 9) | NTX/APAP 3.25 mg/325 mg (N = 3) | NTX 3.25 mg (N = 3) | NTX/APAP 5 mg/325 mg (N = 1) | NTX 5 mg (N = 1) | p-value* |
|---|---|---|---|---|---|---|---|---|---|
| Insomnia-free at baseline-n (%) | 1 | 2 | 5 (24) | 4 (44) | 1 | 1 | 0 | 0 | |
| Insomnia-free at night after dosing-n (%) | 1 | 2 | 17 (81) | 6 (66) | 3 (100) | 2 (66) | 1 (100) | 0 | |
| Change in insomnia-free-n (%) | 0 | 0 | +12 (57) | +2 (22) | +2 | +1 | 1 (100) | 0 | 0.0833 |

*p-value for NTX/APAP 2.25 mg/325 mg vs. NTX 2.25 mg, p-values were not calculated in logistic regression.

TABLE 37 naltrexone/APAP doses and naltrexone doses for insomnia-intensity at baseline and night post-dosing

| Insomnia-intensity | NTX/APAP (1.5 mg/325 mg) (N = 1) | NTX 1.5 mg (N = 3) | NTX/APAP 2.25 mg/325 mg (N = 21) | NTX 2.25 mg (N = 9) | NTX/APAP 3.25 mg/325 mg (N = 3) | NTX 3.25 mg (N = 3) | NTX/APAP 5 mg/325 mg (N = 1) | NTX 5 mg (N = 1) | p-value* |
|---|---|---|---|---|---|---|---|---|---|
| Insomnia-intensity at baseline-n (%) | 0 | 3 | 39 (185) | 14 (155) | 7 | 2 | 2 | 1 | |
| Insomnia-intensity at night after dosing-n (%) | 0 | 1 | 9 (43) | 4 (44) | 0 | 1 | 0 | 3 | |
| Change in insomnia-intensity n (%) | 0 | −2 (−66) | −30 (−142) | −10 (−111) | −7 (−100) | −1 (−50) | −2 (−100) | +2 (+200) | 0.2455 |

Insomnia intensity = sum of severity of all patients.
Insomnia change = n/a, if there was no baseline insomnia
*p-value for NTX/APAP 2.25 mg/325 mg vs. NTX 2.25 mg, p-values were not calculated in logistic regression.

Emotional Pain Data 24-hours after dosing, naltrexone/acetaminophen 2.25 mg/325 mg (N=21) vs. naltrexone 2.25 mg (N=9) for emotional pain-free change from baseline was 42% vs. 33%, and for emotional pain intensity, the change from baseline was (−94%) vs. (−55%). The data suggests beneficial effect of the combination and of naltrexone on emotional pain intensity with advantage for the combination.

TABLE 38 naltrexone/APAP doses and naltrexone doses for emotional pain-free at baseline & at 24 h

| Emotional pain-free | NTX/APAP 1.5 mg/325 mg (N = 1) | NTX 1.5 mg (N = 3) | NTX/APAP 2.25 mg/325 mg (N = 21) | NTX 2.25 mg (N = 9) | NTX/APAP 3.25 mg/325 mg (N = 3) | NTX 3.25 mg (N = 3) | NTX/APAP 5 mg/325 mg (N = 1) | NTX 5 mg (N = 1) |
|---|---|---|---|---|---|---|---|---|
| Emotional pain-free at baseline-n (%) | 1 | 2 | 10 (48) | 6 (66) | 1 | 2 | 0 | 0 |
| Emotional Pain-free at 24 hours after dosing-n (%) | 1 | 3 | 19 (90) | 9 (100) | 3 | 3 | 1 | 1 |
| Change in emotional pain-free-n (%) | 0 | +1 | +9 (+42) | +3 (+33) | +2 (+200) | +1 + (50) | +(1 + 100) | +(1 + 100) |

*Emotional pain-free change = n/a, if there was no baseline emotional pain.
*p-value for NTX/APAP 2.25 mg/325 mg vs. NTX 2.25 mg, p-values were not calculated in logistic regression.

TABLE 39 naltrexone/APAP doses and naltrexone doses for emotional pain-intensity at baseline and 24 h

| Emotional pain-intensity | NTX/APAP 1.5 mg/325 mg (N = 1) | NTX 1.5 mg (N = 3) | NTX/APAP 2.25 mg/325 mg (N = 21) | NTX 2.25 mg (N = 9) | NTX/APAP 3.25 mg/325 mg (N = 3) | NTX 3.25 mg (N = 3) | NTX/APAP 5 mg/325 mg (N = 1) | NTX 5 mg (N = 1) |
|---|---|---|---|---|---|---|---|---|
| Emotional pain-intensity at baseline-n (%) | 0 | 2 | 26 (123) | 5 (55) | 5 | 1 | 2 | 2 |
| Emotional pain-intensity at 24 hours post-dosing-n (%) | 0 | 0 | 6 (29) | 0 | 0 | 0 | 0 | 0 |
| Change in emotional pain-intensity-n (%) | n/a | 2 (−100) | −20 (−94) | −5 (−55) | −5 (−100) | −1 (−100) | −2 (−100) | −2 (−100) |

TABLE 39-continued naltrexone/APAP doses and naltrexone doses for emotional pain-intensity at baseline and 24 h

| Emotional pain-intensity | NTX/APAP 1.5 mg/325 mg (N = 1) | NTX 1.5 mg (N = 3) | NTX/APAP 2.25 mg/325 mg (N = 21) | NTX 2.25 mg (N = 9) | NTX/APAP 3.25 mg/325 mg (N = 3) | NTX 3.25 mg (N = 3) | NTX/APAP 5 mg/325 mg (N = 1) | NTX 5 mg (N = 1) |
|---|---|---|---|---|---|---|---|---|
| p-value NTX/APAP 2.25 mg/325 mg vs. NTX 2.25 mg | | | 0.0117 | | | | | |

Emotional pain-intensity = sum of severity of all patients.
Emotional pain-intensity change = n/a, if there was no baseline emotional pain.
P-value for Naltrexone/APAP 2.25 mg/325 mg vs. Naltrexone 2.25 mg, by comparison of proportions.

CONCLUSION

The migraine pilot study included data for naltrexone alone in 1.5 mg, 2.25 mg, 3.25 mg, and 5 mg doses. The data showed, high efficacy of all dosages of naltrexone alone for treatment of migraine headache physical pain. From 90 minutes to 48 hours headache pain-free was 100% for all dosages. A comparison to results from the literature, (Brandes J L, Kudrow D, Stark S R, et al. Sumatriptan-naproxen for acute treatment of migraine: a randomized trial. JAMA. 2007; 297(13):1443-54) for sumatriptan, the current most effective treatment for migraine, were 2-hour migraine pain-free was 25%, shows superiority of naltrexone. This is a confirmation for the efficacy of naltrexone alone in all the tested dosages for treatment of physical pain of migraine.

The migraine pilot study included data for naltrexone alone for treatment of emotional pain. 24-hour changed from baseline for naltrexone 2.25 mg (n=9) in emotional pain intensity decreased by 55% and emotional pain-free increased by 33%. All other dosages of naltrexone alone also demonstrated emotional pain-free and emotional pain-intensity improvement.

The migraine pilot study included data for naltrexone alone for treatment of insomnia. The night before treatment compared to the night after treatment for naltrexone 2.25 mg (n=9) in insomnia intensity improved by 111% and insomnia-free improved by 22%, demonstrating significant improvement for insomnia for naltrexone alone. All other dosages of naltrexone alone demonstrated improvement in insomnia-free and insomnia-intensity.

The LBP study demonstrated superiority of naltrexone/acetaminophen vs. acetaminophen for physical pain. P-value for naltrexone/acetaminophen vs. acetaminophen alone was 0.0001 for WPI, API, and PRSI. This demonstrates synergism of naltrexone/acetaminophen vs. acetaminophen for physical pain of low back.

The migraine study demonstrated superiority of naltrexone/acetaminophen vs. naltrexone for migraine physical pain, p-value for naltrexone/acetaminophen 2.25 mg/325 mg vs. naltrexone 2.25 mg alone for migraine headache pain-free at 30 minutes was 0.0066, demonstrating synergism for naltrexone/acetaminophen for migraine headache physical pain. All dosages of the combination demonstrated 90-100% pain-free at 2 hours. The migraine study demonstrated superiority of naltrexone/acetaminophen vs. naltrexone for emotional pain, in the migraine pilot study, p-value for Naltrexone/acetaminophen 2.25 mg/325 mg vs. naltrexone alone for emotional pain intensity at 24-hours was 0.017, demonstrating synergism for naltrexone/acetaminophen for emotional pain intensity compared to naltrexone. All dosages of the combination demonstrated emotional pain intensity improvement. The migraine study demonstrates synergism of the combination vs. naltrexone and the LBP study demonstrates synergism of the combination vs. acetaminophen as far physical pain.

The LBP study demonstrated superiority of naltrexone/acetaminophen vs. acetaminophen for emotional pain and insomnia. P-value for naltrexone/acetaminophen 2.25 mg/325 mg vs. acetaminophen 2.25 mg alone for both was 0.0001. This demonstrates synergism of naltrexone/acetaminophen compared to its individual component, acetaminophen, for emotional pain and insomnia.

The migraine study demonstrated superiority of naltrexone/acetaminophen vs. naltrexone for emotional pain intensity and insomnia. P-value for 2.25 mg/325 mg vs. acetaminophen 2.25 mg alone for emotional pain intensity was 0.0117. Insomnia improvements were also significant. This demonstrates synergism of naltrexone/acetaminophen vs. acetaminophen for emotional pain and insomnia.

Comparing results from the literature (Brandes J L, Kudrow D, Stark S R, et al. Sumatriptan-naproxen for acute treatment of migraine: a randomized trial. JAMA. 2007; 297(13):1443-54) to the migraine pilot study data, naltrexone/acetaminophen 2.25 mg/325 mg demonstrated 76% headache pain-free at 30 min compared to 34% for the combination of sumatriptan-naproxen at 2 hours. Naltrexone/acetaminophen reached headache pain-free four times faster and is two times more effective, which is eight times more effective than the combination of two most effective available treatments.

2-hour headache pain-free for sumatriptan alone was 25%, naltrexone/acetaminophen 2.25 mg/325 mg reached headache pain-free four times faster and is three times more effective, which is twelve times better than sumatriptan alone, the current gold standard of migraine treatment.

That which is claimed is:

1. A method for treating emotional pain in a mammal in need thereof, said method comprising
   administering to the mammal a synergistic composition comprising 3.25 mg per day to 40 mg per day naltrexone or a pharmaceutically acceptable salt or solvate thereof, and 325 mg per day to 4000 mg per day acetaminophen or a pharmaceutically acceptable salt or solvate thereof.

2. The method of claim 1, wherein the naltrexone, or pharmaceutically acceptable salt or solvate thereof, is in a sustained release formulation.

3. The method of claim 1, wherein the naltrexone, or a pharmaceutically acceptable salt or solvate thereof, is administered to the mammal at about 3.25 mg to 15 mg per day, and wherein the acetaminophen, or a pharmaceutically acceptable salt or solvate thereof, is administered to the mammal at between about 325 mg to 2000 mg per day.

4. The method of claim 1, wherein the acetaminophen or pharmaceutically acceptable salt or solvate thereof is administered to the mammal at about 325 mg per day, and wherein the naltrexone or pharmaceutically acceptable salt or solvate thereof is administered to the mammal at a dose selected from the group consisting of about 3.25 mg per day and about 5 mg per day.

5. The method of claim 1, wherein the naltrexone or pharmaceutically acceptable salt or solvate thereof is administered to the mammal at about 3.25 mg per day, and wherein the acetaminophen or pharmaceutically acceptable salt or solvate thereof is administered to the mammal at about 325 mg per day.

6. The method of claim 1, wherein the naltrexone or pharmaceutically acceptable salt or solvate thereof is administered to the mammal at about 5 mg per day, and wherein the acetaminophen or pharmaceutically acceptable salt or solvate thereof is administered to the mammal at about 325 mg per day.

7. The method of claim 1, wherein the naltrexone or pharmaceutically acceptable salt or solvate thereof is administered to the mammal at about 9 mg per day, and wherein the acetaminophen or pharmaceutically acceptable salt or solvate thereof is administered to the mammal at about 1300 mg per day.

8. The method of claim 1, wherein the naltrexone or pharmaceutically acceptable salt or solvate thereof is administered to the mammal at about 15 mg per day, and wherein the acetaminophen or pharmaceutically acceptable salt or solvate thereof is administered to the mammal at about 2000 mg per day.

9. The method of claim 1, wherein the combination is administered once, twice, three or four times per day.

10. The method of claim 1, wherein the combination is administered orally.

11. The method of claim 1, wherein the naltrexone, or pharmaceutically acceptable salt or solvate thereof, and the acetaminophen, or pharmaceutically acceptable salt or solvate thereof are formulated into a single fixed combination dosage form.

12. The method of claim 11, wherein the single fixed combination dosage form is in the form of tablets, lozenges, troches, hard candies, or liquids.

13. The method of claim 1, wherein the emotional pain is associated with an emotional disturbance with one or more signs or symptoms selected from the group consisting of abandonment, ambivalence, anger, anguish, betrayal, compulsion, confusion, deterioration, failure, fatigue, fear, grief, guilt, helplessness, hopelessness, horror, hurt feelings, inferiority, insomnia, irritation, loneliness, loss of meaning, lure of death, powerlessness, rejection, sadness, self-hate, shame, terror, and worthlessness.

14. The method of claim 1, wherein the mammal is also experiencing one or more substance abuse or addiction selected from drug abuse, drug addiction, alcohol abuse, and alcohol addiction.

15. The method of claim 1, wherein the mammal is not experiencing substance abuse or addiction selected from drug abuse, drug addiction, alcohol abuse, and alcohol addiction.

16. The method of claim 1, wherein the naltrexone or pharmaceutically acceptable salt or solvate thereof is administered to the mammal at about 6.75-9.75 mg per day, and wherein the acetaminophen or pharmaceutically acceptable salt or solvate thereof is administered to the mammal at about 975 mg per day.

* * * * *